(12) United States Patent
Hansen et al.

(10) Patent No.: US 11,555,050 B2
(45) Date of Patent: *Jan. 17, 2023

(54) OLIGONUCLEOTIDE CONJUGATION PROCESS

(71) Applicant: Roche Innovation Center Copenhagen A/S, Basel (CH)

(72) Inventors: Dennis Jul Hansen, Hørsholm (DK); Christoph Rosenbohm, Hørsholm (DK); Michael Meldgaard, Hørsholm (DK)

(73) Assignee: Roche Innovation Center Copenhagen A/S, Basel (CH)

( * ) Notice: Subject to any disclaimer, the term of this patent is extended or adjusted under 35 U.S.C. 154(b) by 17 days.

This patent is subject to a terminal disclaimer.

(21) Appl. No.: 16/805,618

(22) Filed: Feb. 28, 2020

(65) Prior Publication Data

US 2021/0040137 A1 Feb. 11, 2021

Related U.S. Application Data

(63) Continuation of application No. 15/771,206, filed as application No. PCT/EP2016/073224 on Sep. 29, 2016, now Pat. No. 10,577,388.

(30) Foreign Application Priority Data

Oct. 2, 2015 (EP) ..................................... 15188120

(51) Int. Cl.
| | |
|---|---|
| C07H 17/02 | (2006.01) |
| C07H 21/00 | (2006.01) |
| C07H 1/00 | (2006.01) |
| C07H 19/06 | (2006.01) |
| C07H 19/16 | (2006.01) |
| A61K 47/55 | (2017.01) |
| A61K 47/54 | (2017.01) |
| C07H 21/02 | (2006.01) |
| C07H 21/04 | (2006.01) |

(52) U.S. Cl.
CPC ............ *C07H 21/00* (2013.01); *A61K 47/549* (2017.08); *A61K 47/55* (2017.08); *C07H 1/00* (2013.01); *C07H 19/06* (2013.01); *C07H 19/16* (2013.01); *C07H 21/02* (2013.01); *C07H 21/04* (2013.01)

(58) Field of Classification Search
None
See application file for complete search history.

(56) References Cited

U.S. PATENT DOCUMENTS

| | | | |
|---|---|---|---|
| 5,622,825 | A | 4/1997 | Law et al. |
| 5,994,517 | A | 11/1999 | Ts'o et al. |
| 10,577,388 | B2 | 3/2020 | Hansen et al. |
| 2018/0305392 | A1 | 10/2018 | Hansen et al. |

FOREIGN PATENT DOCUMENTS

| | | |
|---|---|---|
| JP | 2004/500006 | 1/2004 |
| JP | 2012/530059 | 11/2012 |
| WO | WO 99/67423 | 12/1999 |
| WO | WO 2007/031091 | 3/2007 |
| WO | WO 2007/112754 | 10/2007 |
| WO | WO 2008/113832 | 9/2008 |
| WO | WO 2009/043353 | 4/2009 |
| WO | WO 2009/124238 | 10/2009 |
| WO | WO 2009/126933 | 10/2009 |
| WO | WO 2010/144740 | 12/2010 |
| WO | WO 2012/083046 | 6/2012 |
| WO | WO 2012/089352 | 7/2012 |
| WO | WO 2013/033230 | 3/2013 |
| WO | WO 2014/076195 | 5/2014 |
| WO | WO 2014/118267 | 8/2014 |
| WO | WO 2014/118272 | 8/2014 |
| WO | WO 2014/179445 | 11/2014 |
| WO | WO 2014/179620 | 11/2014 |

OTHER PUBLICATIONS

Aaronson et al., "Rapid HATU-Mediated Solution Phase siRNA Conjugation", Bioconjug Chem., Aug. 17, 2011, 22(8):1723-1728.
Bergstrom "Unnatural Nucleosides with Unusual Base Pairing Properties," Current Protocols in Nucleic Acid Chemistry, Jun. 2009 37:1.4.1-1.4.32.
Hangai et al., "In Vivo Delivery of Phosphorothioate Oligonucleotides Into Murine Retina," Arch Ophthalmol., Mar. 1998, 116(3):342-348.
Hangeland et al., "Cell-type specific and ligand specific enhancement of cellular uptake of oligodeoxynucleoside methylphosphonates covalently linked with a neoglycopeptide, YEE(ah-GalNAc)3," Bioconjug Chem., Nov.-Dec. 1995, 6(6):695-701.
Hirao et al, "Natural versus artificial creation of base pairs in DNA: origin of nucleobases from the perspectives of unnatural base pair studies," Accounts of Chemical Research, 2012, 45(12):2055-2065.
Lonnberg, "Solid-Phase Synthesis of Oligonucleotide Conjugates Useful for Delivery and Targeting of Potential Nucleic Acid Therapeutics", Bio Cong., Jun. 17, 2009, 20(6):1065-1094.
Milesi et al., "Synthesis of oligonucleotide conjugates in anhydrous dimethyl sulfoxide," Methods in Enzymology, 1999, 313:164-173.
International Search Report and Written Opinion in International Application No. PCT/EP2016/073224, dated Dec. 8, 2016, 11 pages.
International Preliminary Report on Patentability in International Application No. PCT/EP2016/073224, dated Apr. 3, 2018, 7 pages.

(Continued)

*Primary Examiner* — Patrick T Lewis

(74) *Attorney, Agent, or Firm* — Fish & Richardson P.C.

(57) ABSTRACT

The present invention relates to the field of oligonucleotide conjugates and to methods of synthesis thereof. In the present method a low-water content solvent environment allows a more efficient conjugation, reducing the amount of conjugate moiety needed and increasing the conjugation reaction speed.

1 Claim, 13 Drawing Sheets

Figure 1:
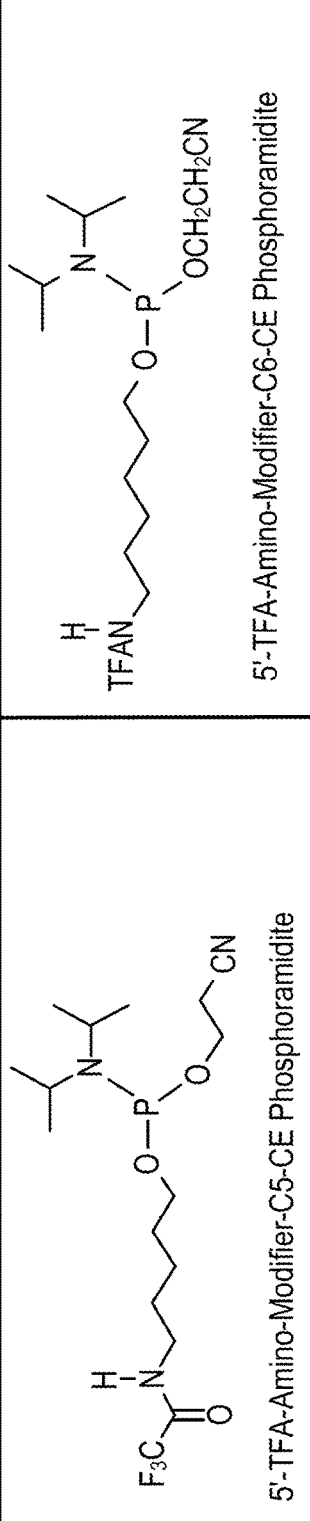
Figure 1:
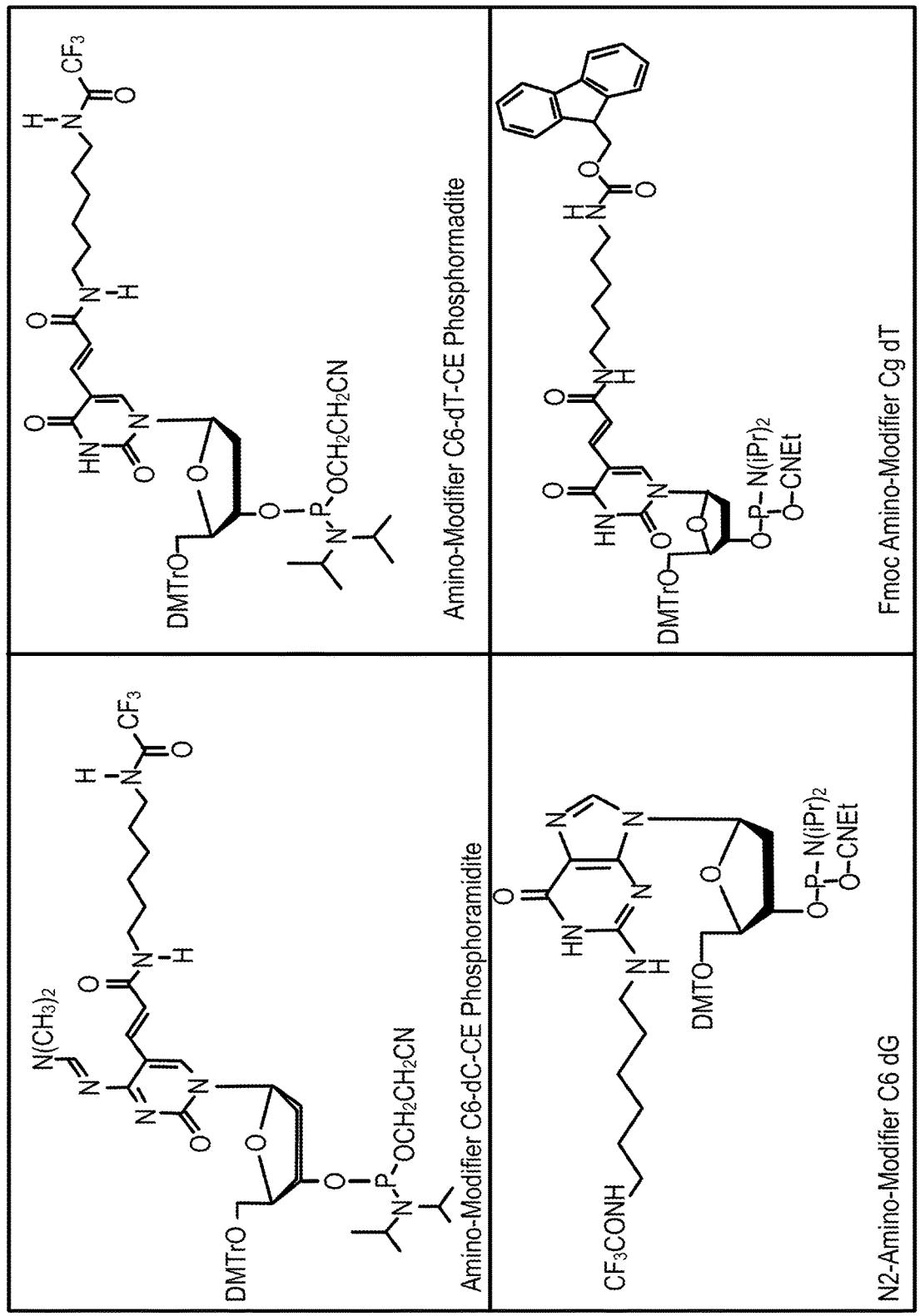
Figure 1:
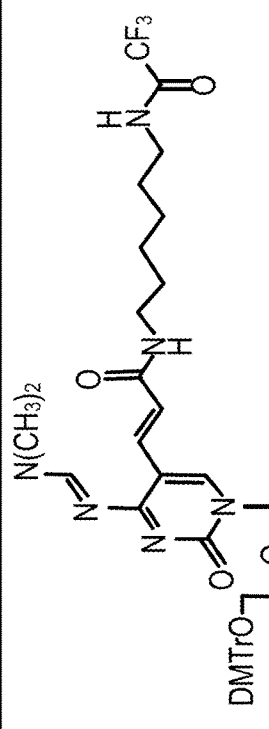
Figure 1:
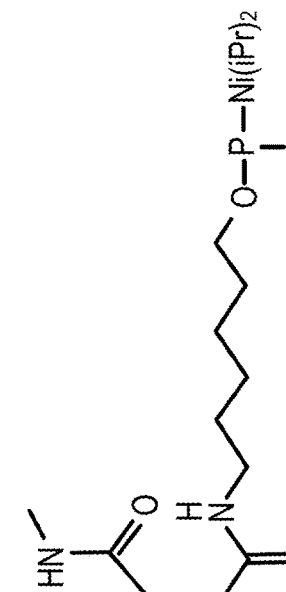

Specification includes a Sequence Listing.

(56) References Cited

OTHER PUBLICATIONS

Ostergaard et al., "Efficient Synthesis and Biological Evaluation of 5'-GalNAc Conjugated Antisense Oligonucleotides," Bioconjugate Chemistry, May 19, 2015, 26(8):1451-1455.
Virta et al., "Solid-supported synthesis of oligomeric bioconjugates", Tetrahedron, Jul. 7, 2003, 59(28):5137-5174.
Murakami et al., "Chemical Syntheses of Functionalized Antisense DNA," Synthetic Organic Chemistry, 1990, 48(3):180-193.

Fluorescein NHS ester (mixture of isomers)

Digoxigenin NHS ester

GalNAc2 NHS ester

OLIGONUCLEOTIDE CONJUGATION PROCESS

FIELD OF THE INVENTION

The present invention relates to the field of oligonucleotide conjugates and to methods of synthesis thereof. In the present method a low-water content solvent environment allows a more efficient conjugation, reducing the amount of conjugate moiety needed and increasing the conjugation reaction speed.

BACKGROUND TO THE INVENTION

Recently there has been considerable focus in the conjugation of oligonucleotides with non-nucleotide moieties which add additional functionality to the oligonucleotide, for example, enabling targeting of therapeutic oligonucleotides to specific organs and tissues in vivo. For targeting to liver hepatocytes trivalent GalNAc conjugation moieties capable of binding to asialoglycoprotein receptors have been found to allow for vastly reduced dosages whilst delivering effective therapeutic action, see for example WO2014/118267. WO 2013/033230 also describes a variety of oligonucleotide conjugates including antibodies, carbohydrates, cholesterol, insulin, PEG, transferrin and vitamins. The manufacture of oligonucleotide conjugates is therefore of major importance, particularly when considering the increased costs of manufacture of the conjugate group and the additional process steps in conjugation.

Milesi et al., Methods in Enzymology (1999) 313, pp 164-173, reports on the synthesis of oligonucleotide conjugates in anhydrous dimethyl sulfoxide. The procedure used by Milesi at al. uses triethylammonium salt to solubilise an 10 bp DNA oligonucleotide in DMSO, prior to conjugation to a lipophilic 5'minor groove binding conjugate, and is recommended for use with lipophilic and hydrostatically unstable groups. According to Milesi et al., 2.5 molar equivalents of conjugate group were used as compared to the oligonucleotide, and typically up to 20 molar equivalents of the conjugate group are used.

STATEMENT OF INVENTION

The invention provides for a process of synthesizing an amide linked oligonucleotide conjugate comprising the step of reacting a conjugate group to a reactive amino group of an oligonucleotide, wherein said reaction step is in a solvent composition comprising at least about 85% (v/v) polar aprotic solvent, and wherein the molar ratio of the conjugate group/oligonucleotide used in the solvent composition is less than about 2, such as between about 0.5 and about 2, and wherein the solvent composition comprises a lipophilic cation.

The invention provides for a process of synthesizing an amide linked oligonucleotide conjugate comprising the step of reacting a conjugate group to a reactive amino group of an oligonucleotide, wherein said reaction step is performed in a solvent composition which comprises at least about 85% dimethyl formamide (DMF) (v/v), and wherein the solvent composition comprises a lipophilic cation.

The invention provides for a process of synthesizing an amide linked oligonucleotide conjugate comprising the step of reacting a conjugate group to a reactive amino group of an oligonucleotide, wherein said reaction step is performed in a solvent composition which comprises at least about 85% polar aprotic solvent (v/v), and, wherein the solvent composition comprises a lipophillic cation comprising at least 1 lipophillic $C_{4-36}$ alkyl group, such as a quaternary ammonium cation comprising at least 1 lipophillic $C_{4-36}$ alkyl group.

The invention provides for a process of synthesizing an amide linked oligonucleotide conjugate comprising the step of reacting a conjugate group to a reactive amino group of an oligonucleotide, wherein said reaction step is performed in a solvent composition which comprises at least about 85% polar aprotic solvent (v/v), wherein the solvent composition comprises a lipophilic cation, and wherein the conjugate group is a non-lipophilic moiety.

The invention provides for a process of synthesizing an amide linked oligonucleotide conjugate comprising the step of reacting a conjugate group to a reactive amino group of an oligonucleotide, wherein said reaction step is performed in a solvent composition which comprises at least about 85% polar aprotic solvent (v/v), wherein the solvent composition comprises a lipophilic cation, and wherein the conjugate group is an asialoglycoprotein receptor ligand.

The invention provides for a process of synthesizing an amide linked oligonucleotide conjugate comprising the step of reacting a conjugate group to a reactive amino group of an oligonucleotide, wherein said reaction step is in a solvent composition comprising at least about 85% (v/v) polar aprotic solvent, and wherein the molar ratio of the conjugate group/oligonucleotide used in the solvent composition is less than about 2, such as between about 0.5 and about 2, wherein the solvent composition comprises a lipophilic cation; wherein the polar aprotic solvent is dimethyl formamide (DMF); and wherein the lipophilic cation is, for example, cetyltrimethylammonium.

The invention provides for a method of synthesizing an oligonucleotide amide linked conjugate comprising the steps of
i) providing a solvent composition comprising a lipophillic cation, a polar aprotic solvent and an oligonucleotide comprising a reactive amino group, and
ii) reacting a conjugate group to the reactive amino group of the oligonucleotide, to produce the oligonucleotide amide linked conjugate;
wherein the solvent composition comprises at least about 85% polar aprotic solvent (v/v), and wherein the molar ratio of conjugate group/oligonucleotide used in step ii) is between about 0.5 and about 2.

The invention provides for a method of synthesizing an oligonucleotide amide linked conjugate comprising the steps of
i) providing a solvent composition comprising a lipophillic cation, a polar aprotic solvent and an oligonucleotide comprising a reactive amino group, and
ii) reacting a conjugate group to the reactive amino group of the oligonucleotide, to produce the oligonucleotide amide linked conjugate;
wherein the solvent composition comprises at least about 85% of the polar aprotic solvent dimethyl formamide (DMF) (v/v).

The invention provides for a method of synthesizing an oligonucleotide amide linked conjugate comprising the steps of
i) providing a solvent composition comprising a lipophillic cation, a polar aprotic solvent and an oligonucleotide comprising a reactive amino group, and
ii) reacting a conjugate group to the reactive amino group of the oligonucleotide, to produce the oligonucleotide amide linked conjugate;

wherein the solvent composition comprises at least about 85% polar aprotic solvent (v/v); and, wherein the lipophilic cation comprises at least 1 lipophilic 1 $C_{4-36}$ alkyl group, such as a quaternary ammonium cation comprising at least 1 lipophilic $C_{4-36}$ alkyl group.

The invention provides for a method of synthesizing an oligonucleotide amide linked conjugate comprising the steps of
i) providing a solvent composition comprising a lipophillic cation, a polar aprotic solvent and an oligonucleotide comprising a reactive amino group, and
ii) reacting a conjugate group to the reactive amino group of the oligonucleotide, to produce the oligonucleotide amide linked conjugate;
wherein the solvent composition of step i) comprises at least about 85% polar aprotic solvent (v/v); and, wherein the conjugate group is a non-lipophilic moiety.

The invention provides for a method of synthesizing an oligonucleotide amide linked conjugate comprising the steps of
i) providing a solvent composition comprising a lipophillic cation, a polar organic solvent and an oligonucleotide comprising a reactive amino group, and
ii) reacting a conjugate group to the reactive amino group of the oligonucleotide, to produce the oligonucleotide amide linked conjugate;
wherein the organic solvent composition of step i) comprises at least about 85% polar aprotic solvent (v/v); and, wherein the conjugate group is an asialoglycoprotein receptor ligand.

The invention provides for a method of synthesizing an oligonucleotide amide linked conjugate comprising the steps of
iii) providing a solvent composition comprising a lipophillic cation, a polar aprotic solvent and an oligonucleotide comprising a reactive amino group, and
iv) reacting a conjugate group to the reactive amino group of the oligonucleotide, to produce the oligonucleotide amide linked conjugate;
wherein the solvent composition comprises at least about 85% of the polar aprotic solvent dimethyl formamide (v/v), and wherein the molar ratio of conjugate group/oligonucleotide used in step ii) is between about 0.5 and about 2, and wherein the lipophillic cation is, for example, cetyltrimethylammonium.

In the above embodiments of the invention the solvent present in the solvent composition may comprise, for example up to about 15%, such as up to about 10% of a protic solvent such as water or an alcohol. In some embodiments, the solvent present in the solvent composition is a mixture of the polar aprotic solvent and a protic solvent such as water or an alcohol. In some embodiments, the solvent present in the solvent composition is a mixture of at least 85% polar aprotic solvent (v/v) and up to about 15% water. In some embodiments, the solvent present in the solvent composition is a mixture of at least 90% polar aprotic solvent (v/v) and up to about 10% water. In some embodiments the solvent present in the solvent composition comprises, for example at least 0.05%, such as at least 0.1%, such as at least 0.5%, such as at least 1% of a protic solvent such as water or an alcohol.

The term method and process are used interchangeably in the description of the invention.

FIGURES

FIG. 1: Examples of commercially available amino-linkers linker phosphoramidites that can be used for synthesis of an oligonucleotide comprising an aliphatic amino group.

Figure 2:
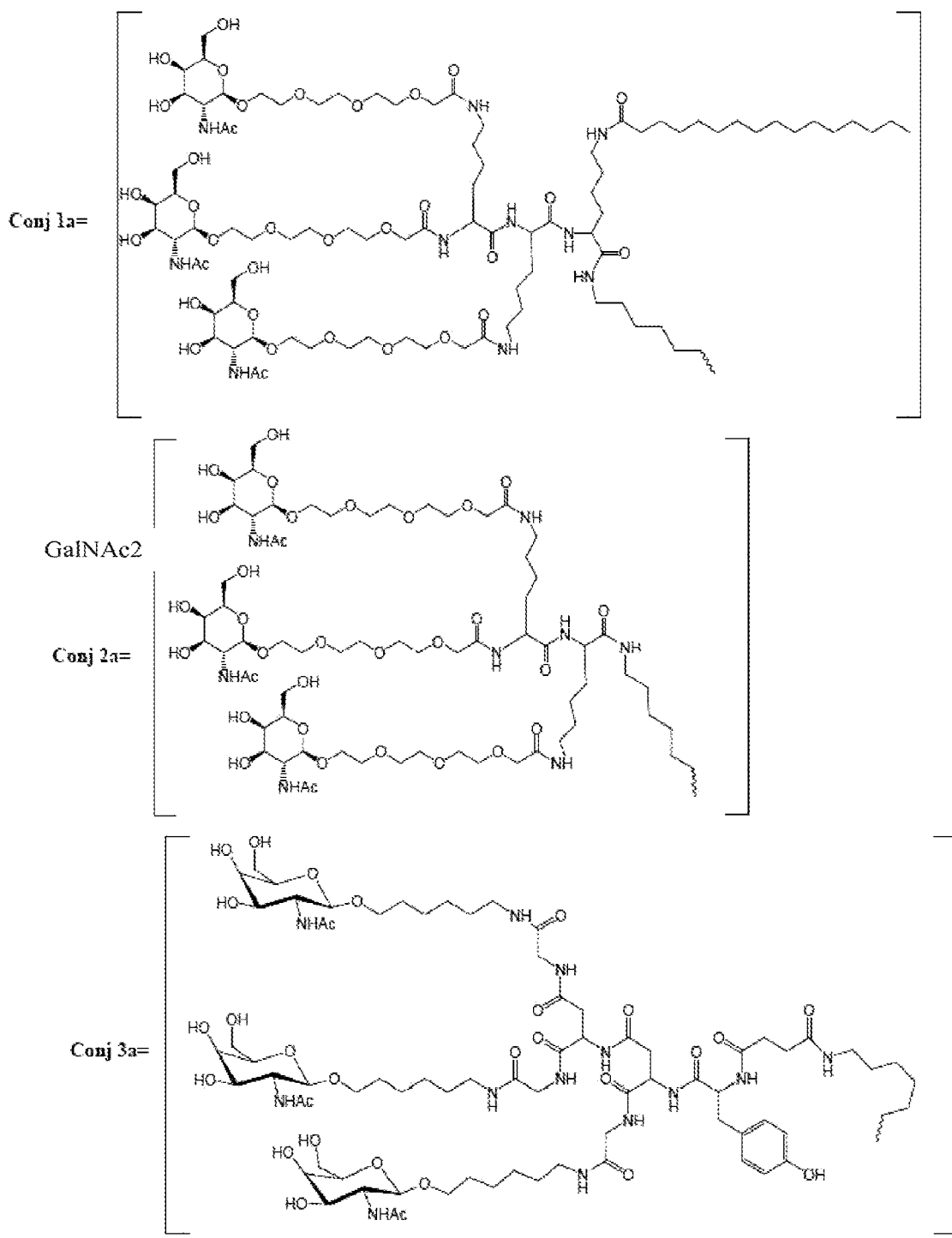

FIG. 2: Examples of GalNAc conjugates. For use in the method of the invention the reactive ester form of these conjugates may be used.

Figure 3:
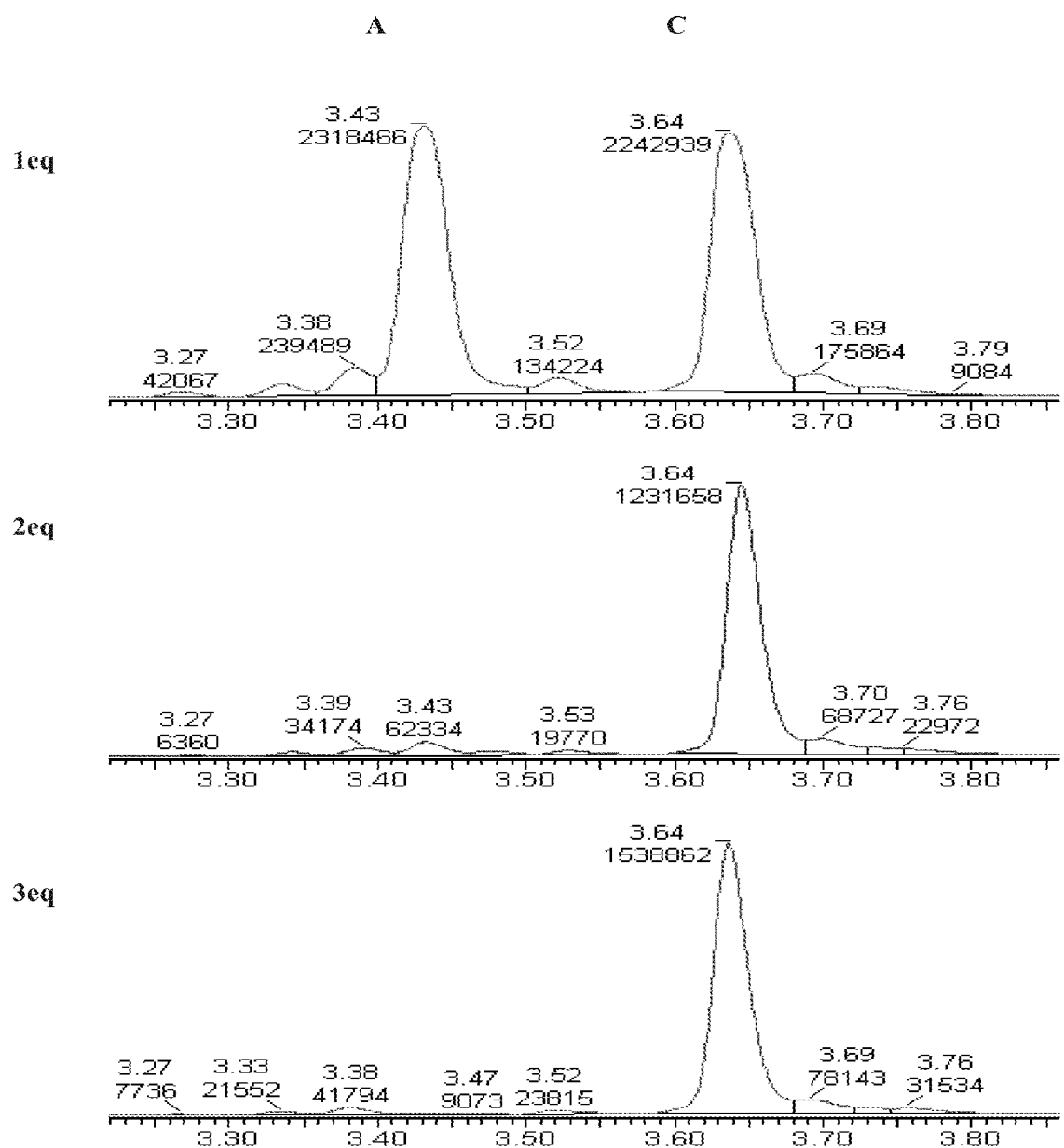

FIG. 3: The normal conversion of the reaction between the aminolabelled-oligonucleotide in aqueous solution and an NHS ester after 2 h. It is clearly seen that, if the oligonucleotide is dissolved in water, there is a need for at least a two times molar excess of the NHS ester relative to the aminolabelled oligonucleotide. A=aminolabelled oligonucleotide, and C=oligonucleotide conjugate.

Figure 4:
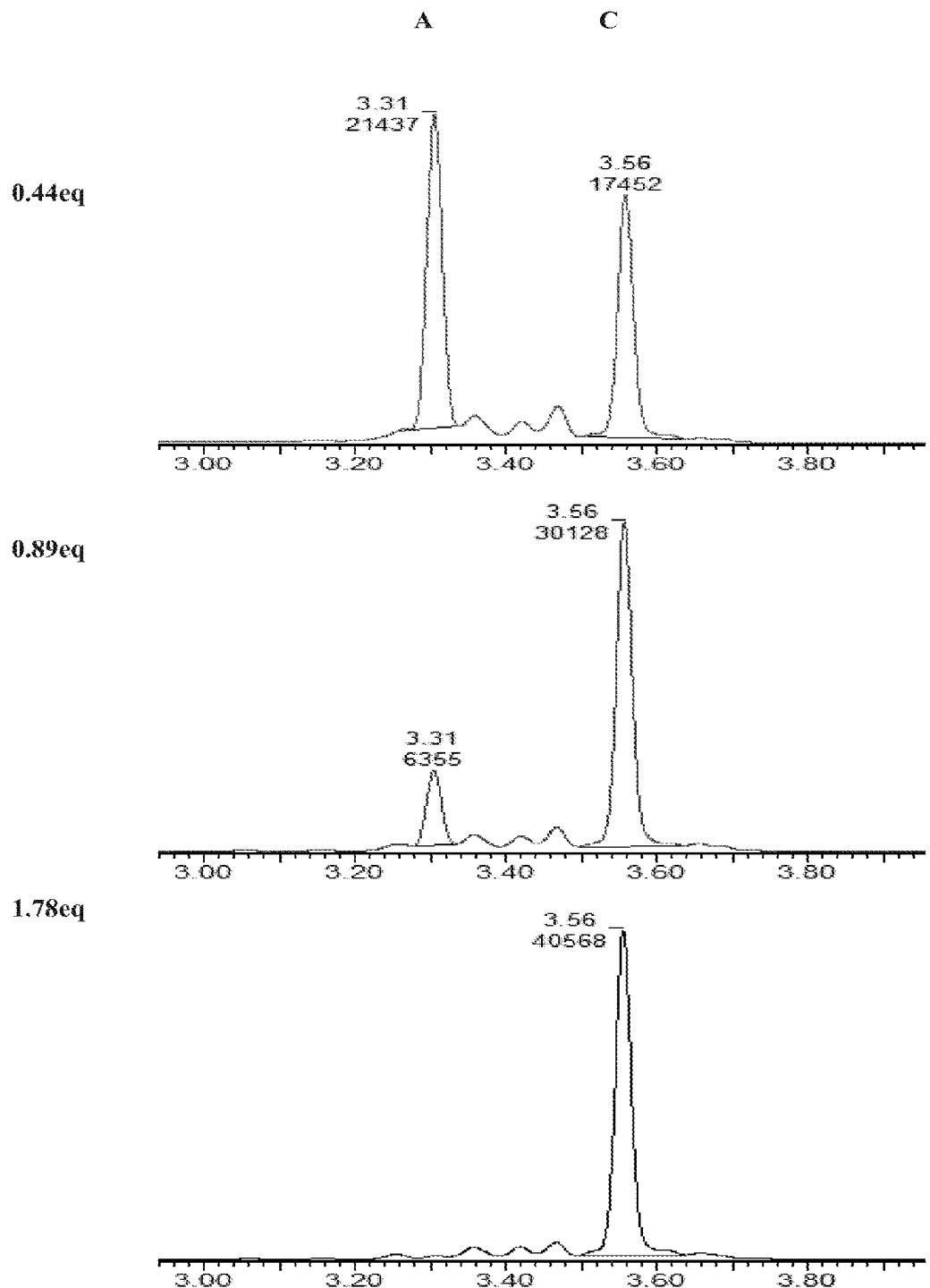

FIG. 4: Conversions of CTA salt of aminolabelled oligonucleotide to GalNAc conjugate in anhydrous DMF after 2 h. Conversions are seen to correlate with the molar equivalent used, thus it is possible to reduce the molar excess of the employed NHS ester. A=aminolabelled oligonucleotide, and C=oligonucleotide conjugate.

Figure 5:
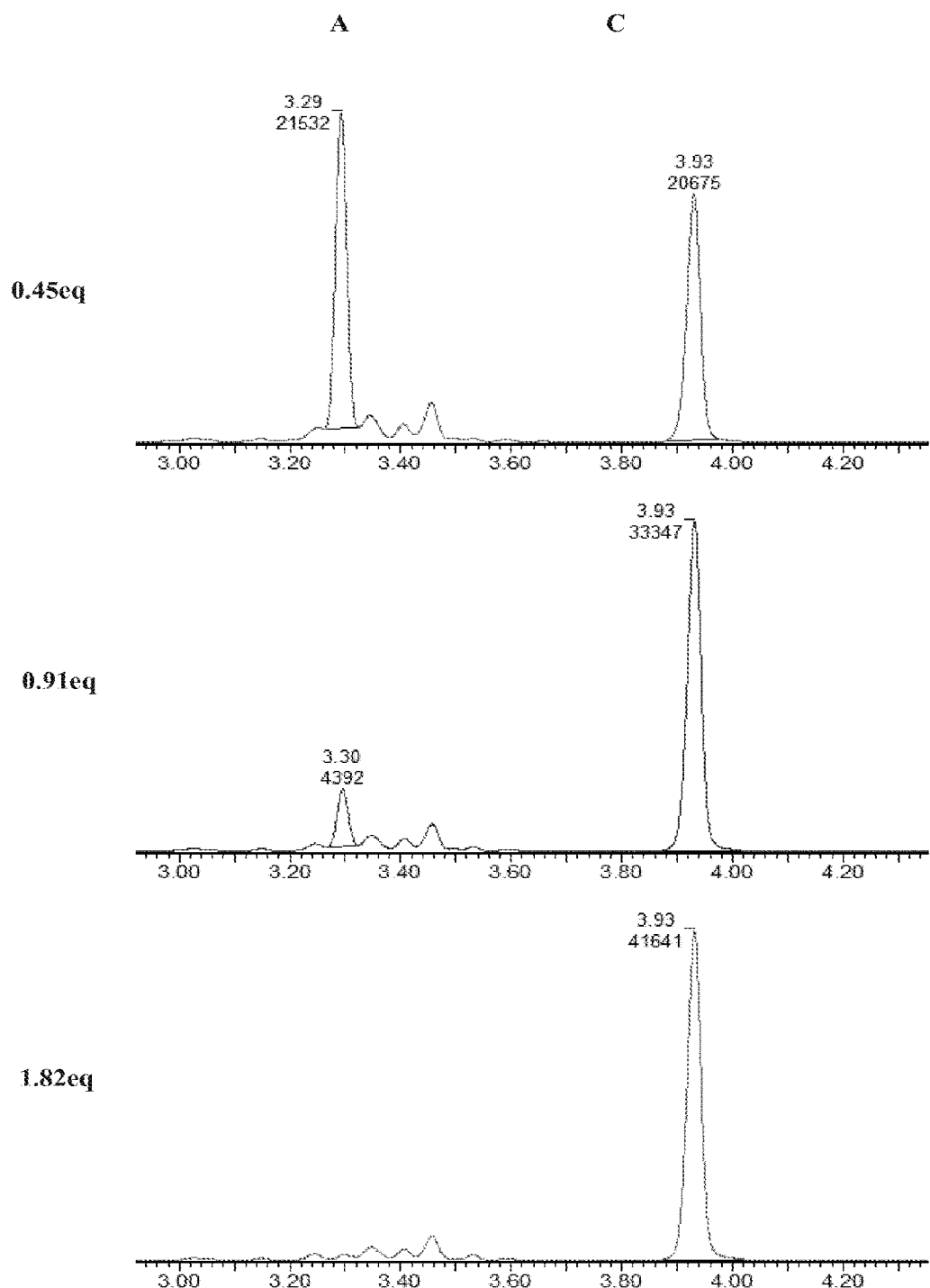

FIG. 5: Conversions of CTA salt of aminolabelled oligonucleotide to Digoxigenin conjugate in anhydrous DMF after 2 h. Conversions are seen to correlate with the molar equivalent used, thus it is possible to reduce the molar excess of the employed NHS ester. This experiments employs a different NHS ester, and thus results in a different conjugate type (digoxigenin). This confirms that the reactions are broadly applicable. A=aminolabelled oligonucleotide, and C=oligonucleotide conjugate.

Figure 6:
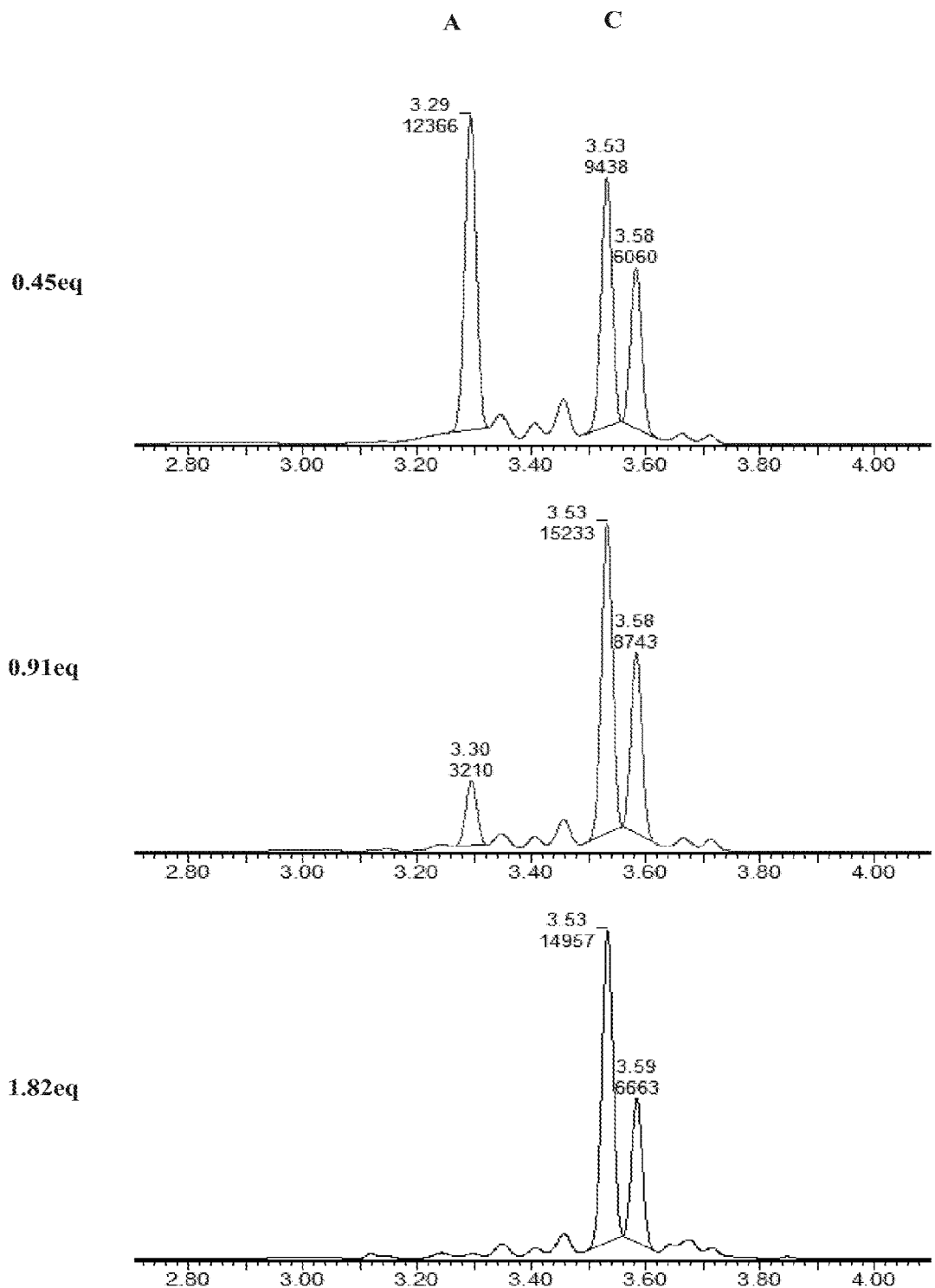

FIG. 6: Conversions of CTA salt of aminolabelled oligonucleotide to fluorescein conjugate in anhydrous DMF after 2 h. Conversions are seen to correlate with the molar equivalent used, thus it is possible to reduce the molar excess of the employed NHS ester. This experiments employs a different NHS ester, and thus results in a different conjugate type (fluorescein). This confirms that the reactions are broadly applicable. There are two product peaks due to the fluorescein NHS ester being a mixture of two isomers. A=aminolabelled oligonucleotide, and C=oligonucleotide conjugate.

Figure 7:
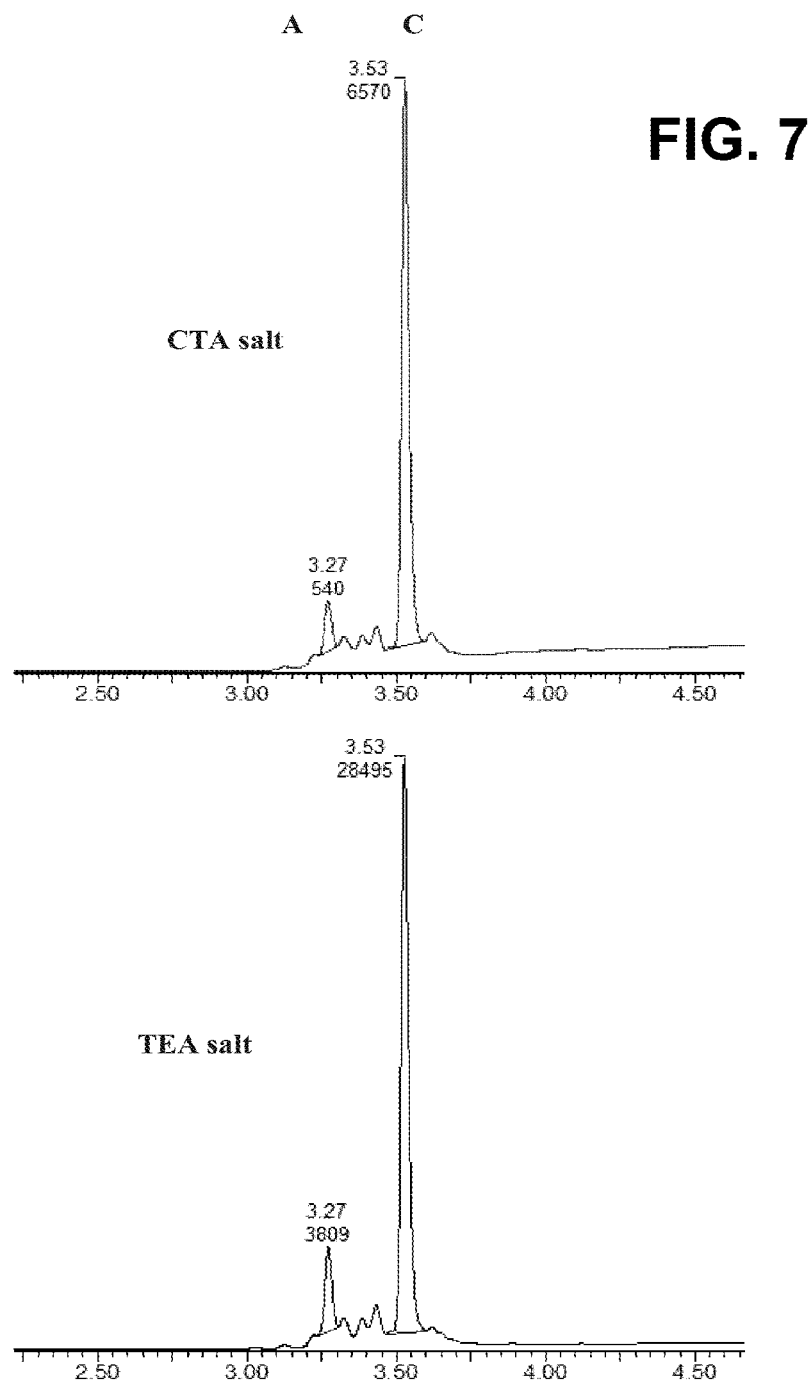
Figure 7:
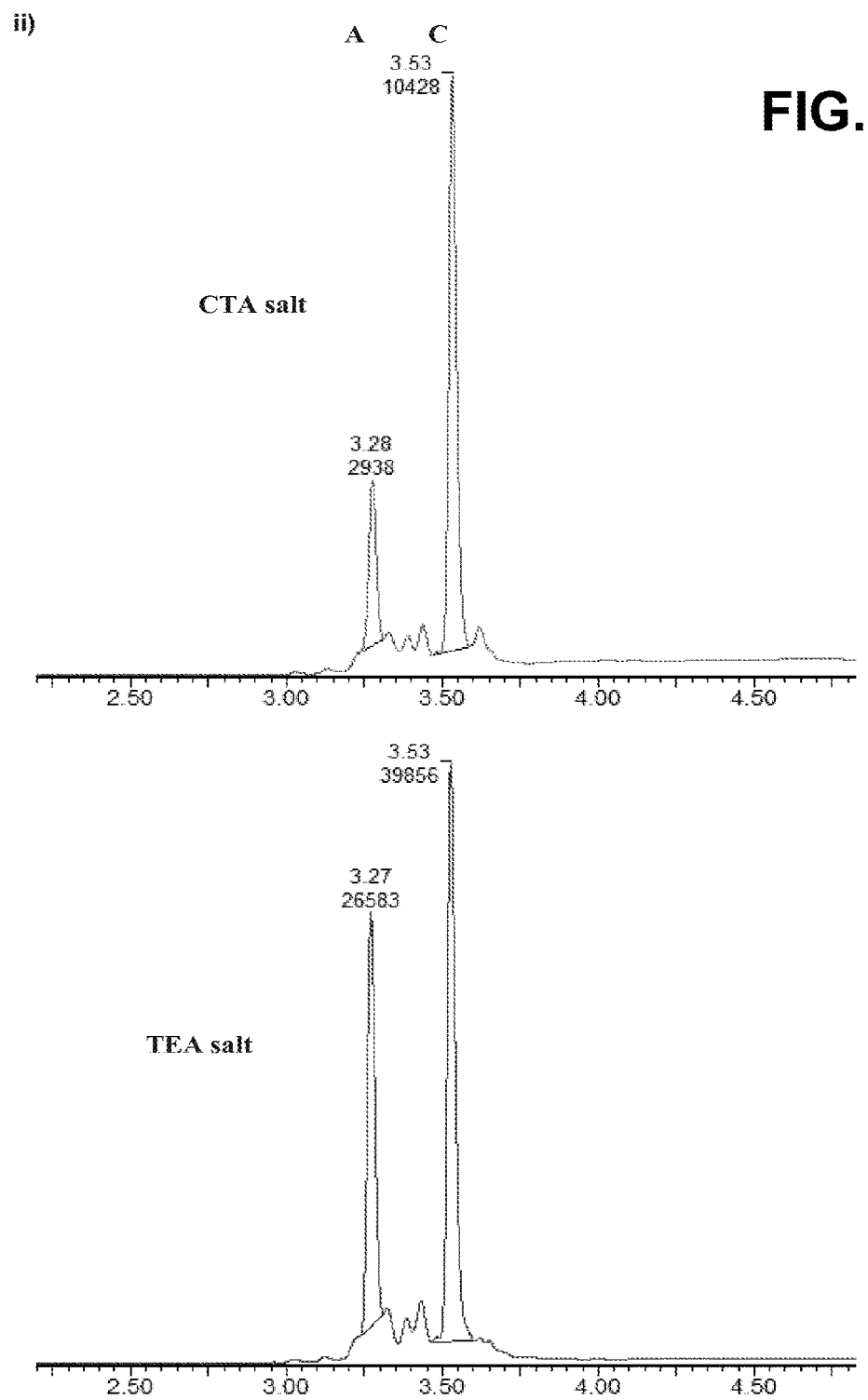

FIG. 7: Comparison of conversions of CTA salt and TEA salt of aminolabelled oligonucleotide to GalNAc conjugate in anhydrous DMF after 1 h (i). Clear kinetic difference between the two salts in DMSO (ii), indicating that the CTA salt is more advantageous. Conversion likewise is improved in DMF for the CTA salt. After 24 h full conversion is observed in all cases. A=aminolabelled oligonucleotide, and C=oligonucleotide conjugate.

Figure 8:
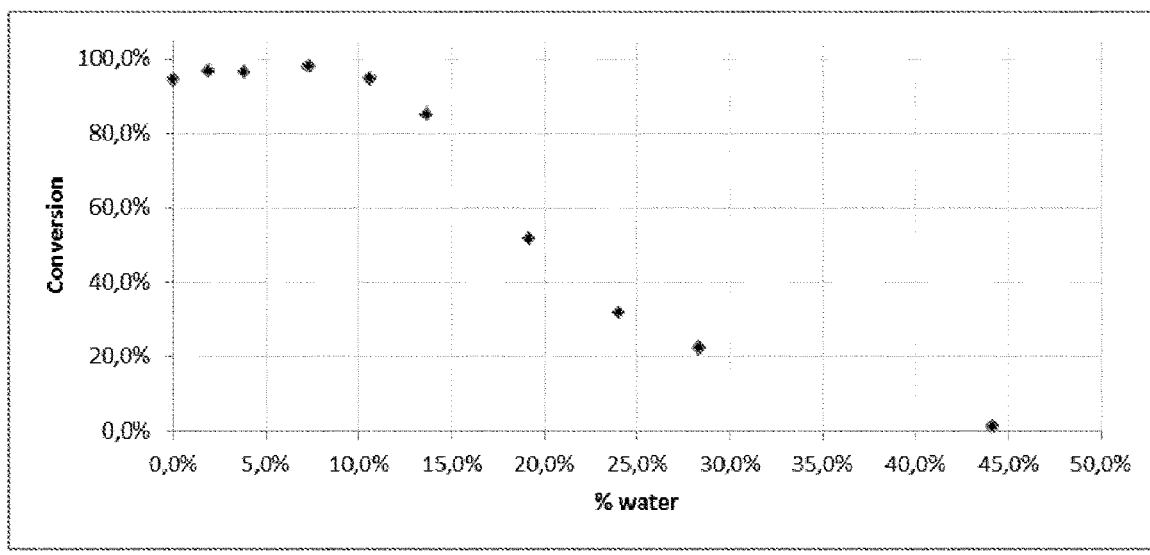
Figure 9:
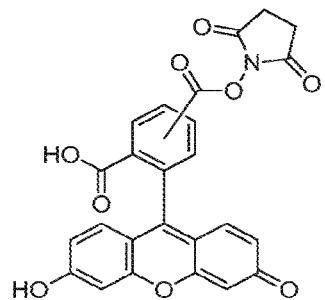
Figure 9:
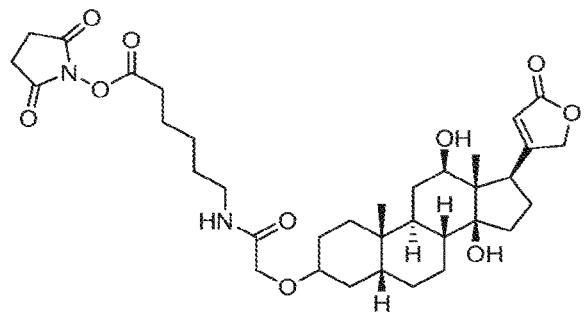
Figure 9:
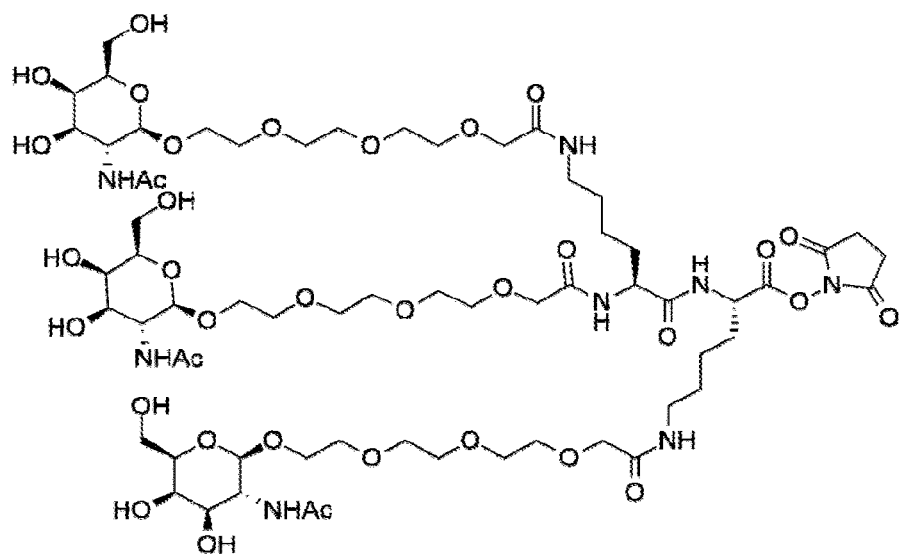

FIG. 8: The Effect of Water content on the efficacy of Oligonucleotide Conjugation FIG. 9 Structures of NHS esters used in the examples and which may, for example, be used in the conjugation reaction of the invention.

DETAILED DESCRIPTION

The invention provides for numerous advantages in the art of oligonucleotide conjugation, providing a more efficient use of the conjugate group as well as improving the rate of conjugation, achieved when using solvents which comprise no water or a small proportion of water.

The Oligonucleotide

The term "oligonucleotide" as used herein is defined as it is generally understood by the skilled person as a molecule comprising two or more covalently linked nucleosides. Such covalently bound nucleosides may also be referred to as nucleic acid molecules or oligomers. Oligonucleotides are commonly made in the laboratory by solid-phase chemical synthesis followed by purification. When referring to a sequence of the oligonucleotide, reference is made to the sequence or order of nucleobase moieties, or modifications thereof, of the covalently linked nucleotides or nucleosides. The oligonucleotide of the invention is man-made, and is chemically synthesized, and is typically purified or isolated. The oligonucleotide of the invention may comprise one or more modified nucleosides or nucleotides. In some embodiments, the oligonucleotide is an antisense oligonucleotide The term "Antisense oligonucleotide" as used herein is defined as oligonucleotides capable of modulating expression of a target gene by hybridizing to a target nucleic acid, in particular to a contiguous sequence on a target nucleic acid. The antisense oligonucleotides are not essentially double stranded and are therefore not siRNAs. Preferably, the antisense oligonucleotides of the present invention are single stranded.

The oligonucleotide may be a modified oligonucleotide. The term modified oligonucleotide describes an oligonucleotide comprising one or more sugar-modified nucleosides and/or modified internucleoside linkages. The term chimeric" oligonucleotide is a term that has been used in the literature to describe oligonucleotides with modified nucleosides.

In some embodiments the oligonucleotide of the method of the invention is an antisense oligonucleotide, an LNA oligonucleotide or a gapmer oligonucleotide.

In a non-limiting embodiment, the oligonucleotide may be selected from the group consisting of:

SEQ ID NO 1
5'-caG$_s$$^m$C$_s$G$_s$t$_s$a$_s$a$_s$a$_s$g$_s$a$_s$g$_s$a$_s$G$_s$G-3'

SEQ ID NO 2
5'-caG$_s$$^m$C$_s$G$_s$t$_s$a$_s$a$_s$a$_s$g$_s$a$_s$g$_s$a$_s$G$_s$T-3'

SEQ ID NO 3
5'-caG$_s$$^m$C$_s$G$_s$t$_s$a$_s$a$_s$a$_s$g$_s$a$_s$g$_s$A$_s$G$_s$G-3' wherein uppercase letters denote beta-D-oxy-LNA units; lowercase letters denote DNA units; the subscript "s" denotes a phosphorothioate linkage: superscript m denotes a DNA or beta-D-oxy-LNA unit containing a 5-methylcytosine base. The oligonucleotides may further comprise a 5' amino hexyl linker. These may for example be used in the method of the invention with a GalNAc conjugate (e.g. an NHS activated ester of GalNAc2) to form the following conjugates:

SEQ ID NO 1
5'-GN2-C6-caG$_s$$^m$C$_s$G$_s$t$_s$a$_s$a$_s$a$_s$g$_s$a$_s$g$_s$a$_s$G$_s$G-3'

SEQ ID NO 2
5'-GN2-C6'-caG$_s$$^m$C$_s$G$_s$t$_s$a$_s$a$_s$a$_s$g$_s$a$_s$g$_s$a$_s$G$_s$T-3'

SEQ ID NO 3
5'-GN2-C6-caG$_s$$^m$C$_s$G$_s$t$_s$a$_s$a$_s$a$_s$g$_s$a$_s$g$_s$A$_s$G$_s$G-3'

GN2-C6 denotes a GalNAc2 carrier component with a $C_6$ linker (shown in FIG. 2).

Other exemplary oligonucleotides include:
5'-AM-C6-G$_s$T$_s$t$_s$g$_s$a$_s$c$_s$a$_s$c$_s$c$_s$t$_s$g$_s$T$_s$$^m$C-3' (SEQ ID NO 4, Compound 1, comprising a 5' aminohexyl linker).

The Oligonucleotide Comprising an Amino Linker

The oligonucleotide provided in step i) of the method of the invention comprises a covalently attached amino group, which may also be referred to as a reactive amino group, which may be suitably in the form of an amino linker. The reactive amino group or amino linker may be attached on any suitable group of the oligonucleotide, for example at the 5' or 3' terminal groups. The amino group may be an aliphatic amino group. The amino linker may, for example, be an amino-alkyl linker or an ethylene glycol linker. In some embodiments the amino linker is a $C_{2-12}$ aminoalkyl linker, for example an aminohexyl linker.

Exemplary amino linkers may be selected from the group of 5'-Amino-Modifier-$C_{12}$, Amino-Modifier $C_2$, Amino-Modifier $C_6$, $N_2$-Amino-Modifier $C_6$, 3'-Amino-Modifier $C_7$, 3'-Amino-Modifier $C_6$ 3'-PT-Amino-Modifier $C_6$; or PC S-Amino-Modifier, 5'-Amino-Modifier TEG, Amino-Modifier Serinol, & 3'-Amino-Modifier Serinol.

FIG. 1 illustrates some commercially available amino linkers which may be used in the synthesis of the oligonucleotide used in the invention.

An aliphatic amino group is an amino group where there are no aromatic rings directly on the nitrogen atom, and is therefore typically a non-nucleosidic amino group. A nucleosidic amino group is an amino group where the nitrogen atom of the amino group is directly bound to the aromatic ring of a purine or pyrimidine base.

The aliphatic amino group may be a primary or a secondary amino group.

In some embodiments, the aliphatic amino group is selected from the group consisting of an amino alkyl, alkylamino alkyl, piperidine, piperazine, pyrrolidine, and imidazole.

The Lipophillic Cation

The use of a lipohillic cation in the solvent composition allows for the solubilisation of the oligonucleotide in the organic solvent composition. The lipohillic cation is typically added into the solvent in the form of a lipophilic salt. The lipophilic salt comprises the lipophilic cation and a suitable anion. Examples of suitable lipophillic cations include quaternary ammonium cations, which comprise at least one lipophillic substituent, such as an alkyl group. Another example of a suitable lipophilic cation is quaternary phosphonium cation which comprise at least one lipophillic substituent, such as an alkyl group. In some embodiments, the lipophilic cation, such as the quaternary ammonium/phosphonium cation, comprises 1, 2, 3 or 4 lipophillic substituents, such as 1, 2, 3 or 4 alkyl groups. In some embodiments, the total number of carbon atoms present in the total of lipophilic substituents is more than 6, such as 7-40. In some embodiments, the total number of carbon atoms present on each of the lipophilic substituents (e.g. alkyl substituent) is 2 or more, such as 3 or more, such as 4 or more. In some embodiments, the total number of carbon atoms present on at least one, e.g. 1, 2, 3 or 4, of the lipophilic substituents (e.g. alkyl substituent) is 2 or more, such as 2-36, 4-36 or 6-36. In some embodiments the lipophilic cation is a triethylammonium cation. However, in the present invention it has been found that using lipophilic cations with longer alkyl chains are useful, for example C4-36 or C6-36 alkyl groups, e.g. C6, C7, C8, C9, C10, C11, C12, C13, C14, C15, C16, C17, C18, C19, C20, C21, C22, C23, C24, C25, C26, C27, C28, C29, C30, C31, C32, C33, C34, C35 and C36. In some embodiments, the lipophilic cation comprises at least 1 C4-36 alkyl group. In some embodiments, the lipophilic cation comprises only 1 C4-C36 or C6-C36 alkyl group. In some embodiments, the lipophilic cation comprises 2 C4-C36 or C6-C36 alkyl groups. In some embodiments, the lipophilic cation comprises 3 C4-C36 or C6-C36 alkyl groups. In some embodiments the lipophilic cation is a quaternary ammonium or phosphonium ion which comprises at least 1 C4-36 alkyl group, and optionally up to 3 other alkyl groups such as C1-3, such as methyl). In some embodiments, the at least 1 C4-36 alkyl is a C8-C24 alkyl, such as a C12-C20 alkyl, such as a C16 alkyl. In some embodiments the lipophilic cation is hexadecyltrimethylammonium (cetyltrimethylammonium) or tetrabutylammonium.

The lipophillic salt further comprises a suitable anion, which may for example be a simple ion, such as a halogen ion, for example bromine or chlorine ions.

Other suitable anions include sulfonate anions, such as tosylate, mesylate; or carboxylate. In some embodiments, the lipophillic salt is selected from the group consisting of cetyl trimethylammonium bromide (CTAB), and cetyl trimethylammonium chloride.

The amount of lipophillic cation in the solvent composition is dependent upon the solvent, salt and oligonucleotide used. In some embodiments, at least about 0.5 molar equivalents of the lipophilic cation are used per phosphorus internucleoside linkage (e.g. phosphodiester, phosphorothioate or phosphorodithioate) present in the oligonucleotide are used. In some embodiments, at least about 0.7 molar equivalents of the lipophilic cation are used per phosphorus internucleoside linkage (e.g. phosphodiester, phosphorothioate or phosphorodithioate) present in the oligonucleotide are used. In some embodiments, at least about 1 molar equivalent of the lipophilic cation are used per phosphorus internucleoside linkage (e.g. phosphodiester, phosphorothioate or phosphorodithioate) present in the oligonucleotide are used. It will be recognised that similar molar equivalents of lipophillic cation may be used for other non phosphorus internucleoside linkages, and may also be applied to the molar equivalents of lipophilic salts. In some embodiments the concentration of the lipophilic cation present in the solvent composition is between 1 mM and 1M, such as between 10 mM and 300 mM.

The Solvent

The solvent used in the solvent composition of the process of the invention is either a polar aprotic solvent, or comprises at least about 85% polar aprotic solvent, such as at least 90% or at least 95% or at least 99% polar aprotic solvent (v/v). The solvent may be selected for its ability to solubilise the lipophilic cation and the oligonucleotide. Solvents are generally classified by the polarity, and considered either polar or non-polar, as indicated by the dielectric constant. Generally, solvents with dielectric constants greater than about 5 are considered "polar" and those with dielectric constants less than 5 are considered "non-polar.

A protic solvent is a solvent which contains labile H+ has a hydrogen atom bound to an oxygen (hydroxyl group) or a nitrogen (amino group), and which readily donate protons to reagents. Conversely, an aprotic solvent does not contain labile H+ or does not readily donate protons to reagents. The solvent composition used in the method of the invention may contain a small amount of a polar protic solvent (e.g. water or an alcohol such as ethanol or methanol), for example up to 15% (v/v) or up to 10% (v/v). In some embodiments the solvent composition does not comprise an organic polar protic solvent.

In the some embodiments of the invention the solvent present in the solvent composition may comprise, for example up to about 15%, such as up to about 10% of a protic solvent such as water or an alcohol. In some embodiments, the solvent present in the solvent composition is a mixture of the polar aprotic solvent and a protic solvent such as water or an alcohol. In some embodiments, the solvent present in the solvent composition is a mixture of at least 85% polar aprotic solvent (v/v) and up to about 15% water. In some embodiments, the solvent present in the solvent composition is a mixture of at least 90% polar aprotic solvent (v/v) and up to about 10% water.

The polar aprotic solvent used in the solvent composition may be selected for its ability to solubilise the oligonucleotide and the lipophilic salt. Exemplary solvents include Dimethyl sulfoxide (DMSO) and Dimethylformamide (DMF). As illustrated in the examples, DMF is a particularly interesting solvent for use in the method of the invention. Other solvents which may be used in some embodiments, include dimethyl acetamide and sulfolane. In some embodiments, the solvent composition comprises DMSO or DMF. In some embodiments the solvent used in the solvent composition is DMSO or DMF, optionally with up to 15% protic solvent (such as water or an alcohol, e.g. ethanol or methanol), such as up to 10% protic solvent (such as water or an alcohol, e.g. ethanol or methanol), present.

In some embodiments the solvent used in the solvent composition is DMSO or DMF, optionally with up to 15% water, such as up to 10% water present.

In some embodiments the solvent composition provided in the process of the invention are essentially anhydrous, for example comprise less than 0.1% water, Such as less than 0.01% water, such as 0.005% water or less. In some embodiments the solvent composition comprises more than 0.01% water, such as more than 0.1% water, such as more than 0.1% water, such as more then 0.5% water. Anhydrous DMF and DMSO as sold by Sigma Aldrich contain less than 0.005% water.

In some embodiments, a small amount of water. (or an alternative protic solvent, such as an alcohol, such as ethanol or methanol) is acceptable in the organic solvent composition. Indeed as illustrated in the examples, the presence of a small amount of a protic solvent, such as water, may improve the conversion rate. For example in some embodiments the solvent composition/reaction conditions may comprise less than 15% water (or in some embodiments an alternative protic solvent such as an alcohol, e.g. ethanol or methanol) such as less than 14%, or less than 13%, or less than 12%, or less than 11%, or less than 10%, or less than 9%, or less than 8%, or less than 7%, or less than 6%, or less than 5%, or less than 4%, or less than 3%, or less than 2%, or less than 1%. Water content is measured based volume of water/volume of polar aprotic solvent. Protic solvent content is measured based volume of protic solvent/volume of polar aprotic solvent. In some embodiments, the solvent composition/reaction conditions comprises at least 0.1% water, such as at least 0.5% water, such as at least 1% water, such as at least 2% water, such as at least 3% water. In some embodiments the solvent composition/reaction conditions comprises between 0% and 10% water, such as between 0% and 10% water, such as between 0% and 9% water, such as between 0% and 8% water, such as between 0% and 7% water, such as between 0% and 6% water, such as between 0% and 5% water, such as between 0% and 4% water, such as between 0% and 3% water, and between 0% and 2% water. In some embodiments the solvent composition/reaction conditions comprises between 0.01% and 10% water, such as between 0.01% and 10% water, such as between 0.01% and 9% water, such as between 0.01% and 8% water, such as between 0.01% and 7% water, such as between 0.01% and 6% water, such as between 0.01% and 5% water, such as between 0.01% and 4% water, such as between 0.01% and 3% water, and between 0.01% and 2% water. In some embodiments the solvent composition/reaction conditions comprises between 0.1% and 10% water, such as between 0.1% and 10% water, such as between 0.1% and 9% water, such as between 0.1% and 8% water, such as between 0.1% and 7% water, such as between 0.1% and 6% water, such as between 0.1% and 5% water, such as between 0.1% and 4% water, such as between 0.1% and 3% water, and between 0.1% and 2% water. In some embodiments the solvent composition/reaction conditions comprises between 0.5% and 10% water, such as between 0.5% and 9% water, such as between 0.5% and 8% water such as between 0.5% and 7% water, such as between 0.5% and 6% water, such as between 0.5% and 5% water, such as between 0.5% and 4% water, such as between 0.5% and 3% water, and between 0.5% and 2% water. In some embodiments the solvent composition/reaction conditions comprises between 1% and 10% water, such as between 1% and 9% water, such as between 1% and 8% water, such as between 1% and 7% water, such as between 1% and 6% water, such as between 1% and 5% water, such as between 1% and 4% water, such as between 1% and 3% water, and between 1% and 2% water. In some embodiments the solvent composition/reaction conditions comprises between 2% and 10% water, such as between 2% and 9% water, such as between 2% and 8% water, such as between 2% and 7% water, such as between 2% and 6%, such as between 2% and 5%, such as between 2% and 4% water, such as between 2% and 3% water. It will be recognised that in some embodiments the % given refer to the exact values, whereas in other embodiments the % s refer to an about value, i.e. optionally providing a +/−10% variance around the absolute values. Furthermore, it will be recognised that in some embodiments, an alternative protic solvent may be used, such as an alcohol such as ethanol or methanol in place of part of or essentially all of the water.

In some embodiments, the solvent composition/reaction conditions comprises at least 0.1% protic solvent, such as at least 0.5% protic solvent, such as at least 1% protic solvent, such as at least 2% protic solvent, such as at least 3% protic solvent. In some embodiments the solvent composition/reaction conditions comprises between 0% and 10% protic solvent, such as between 0% and 10% protic solvent, such as between 0% and 9% protic solvent, such as between 0% and 8% protic solvent, such as between 0% and 7% protic solvent, such as between 0% and 6% protic solvent, such as between 0% and 5% protic solvent, such as between 0% and 4% protic solvent, such as between 0% and 3% protic solvent, and between 0% and 2% protic solvent. In some embodiments the solvent composition/reaction conditions comprises between 0.01% and 10% protic solvent, such as between 0.01% and 10% protic solvent, such as between 0.01% and 9% protic solvent, such as between 0.01% and 8% protic solvent, such as between 0.01% and 7% protic solvent, such as between 0.01% and 6% protic solvent, such as between 0.01% and 5% protic solvent, such as between 0.01% and 4% protic solvent, such as between 0.01% and 3% protic solvent, and between 0.01% and 2% protic solvent. In some embodiments the solvent composition/reaction conditions comprises between 0.1% and 10% protic solvent, such as between 0.1% and 10% protic solvent, such as between 0.1% and 9% protic solvent, such as between 0.1% and 8% protic solvent, such as between 0.1% and 7% protic solvent, such as between 0.1% and 6% protic solvent, such as between 0.1% and 5% protic solvent, such as between 0.1% and 4% protic solvent, such as between 0.1% and 3% protic solvent, and between 0.1% and 2% protic solvent. In some embodiments the solvent composition/reaction conditions comprises between 0.5% and 10% protic solvent, such as between 0.5% and 9% protic solvent, such as between 0.5% and 8% protic solvent such as between 0.5% and 7% protic solvent, such as between 0.5% and 6% protic solvent, such as between 0.5% and 5% protic solvent, such as between 0.5% and 4% protic solvent, such as between 0.5% and 3% protic solvent, and between 0.5% and 2% protic solvent. In some embodiments the solvent composition/reaction conditions comprises between 1% and 10% protic solvent, such as between 1% and 9% protic solvent, such as between 1% and 8% protic solvent, such as between 1% and 7% protic solvent, such as between 1% and 6% protic solvent, such as between 1% and 5% protic solvent, such as between 1% and 4% protic solvent, such as between 1% and 3% protic solvent, and between 1% and 2% protic solvent. In some embodiments the solvent composition/reaction conditions comprises between 2% and 10% protic solvent, such as between 2% and 9% protic solvent, such as between 2% and 8% protic solvent, such as between 2% and 7% protic solvent, such as between 2% and 6%, such as between 2% and 5%, such as between 2% and 4% protic solvent, such as between 2% and 3% protic solvent. The protic solvent is able to solubilize both the lipophilic salt or cation, and the oligonucleotide, either alone, or when part of the solvent composition. In some embodiments the protic solvent is selected from the group consisting of water and alcohol (such as ethanol or methanol) or a mixture thereof. In some embodiments the protic solvent is an alcohol, such as ethanol or methanol or propanol.

The Conjugate Group

The term "conjugate" is intended to indicate a heterogenous molecule formed by the covalent attachment ("conjugation") of the oligonucleotide as described herein to one or more non-nucleotide, or non-polynucleotide moieties. The conjugate group comprises or is a non-nucleotide or non-polynucleotide moiety. The term conjugate group and conjugate moiety may be used interchangeably herein.

In some embodiments, the conjugate group comprises or is a carbohydrate, a non-nucleosidic carbohydrate, or a carbohydrate complex. In some embodiments, the carbohydrate is selected from the group consisting of galactose, lactose, n-acetylgalactosamine, mannose, and mannose-6-phosphate.

In some embodiments, the conjugate group comprises or is selected from the group of protein, glycoproteins, polypeptides, peptides, antibodies, enzymes, and antibody fragments.

In some embodiments, the conjugate group is a lipophilic moiety such as a moiety selected from the group consisting of lipids, phospholipids, fatty acids, and sterols.

In some embodiments, the conjugate group is selected from the group consisting of small molecules drugs, toxins, reporter molecules, and receptor ligands.

In some embodiments the conjugate group is or comprises a vitamin. Water soluble vitamins include thiamine, riboflavin, nicotinic acid or niacin, the vitamin B6 pyridoxal group, pantothenic acid, biotin, folic acid, inositol, choline and ascorbic acid. Lipid soluble vitamins include the vitamin A family, vitamin D, the vitamin E tocopherol family and vitamin K (and phytols).

In some embodiments the reporter molecule is selected from digoxigenin and fluorescein. Other reporter molecules which may be used include fluorescent probes, or fluorescent proteins such as GFP, or enzymatic reporter proteins such as luciferase.

In some embodiments, the conjugate group is a polymer, such as polyethyleneglycol (PEG), polypropylene glycol.

In some embodiments the conjugate group is or comprises an asialoglycoprotein receptor targeting moiety, which may include, for example galactose, galactosamine, N-formyl-galactosamine, N-acetylgalactosamine, N-propionyl-galactosamine, N-n-butanoyl-galactosamine, and N-isobutanoyl-galactos-amine. In some embodiments the conjugate group comprises a galactose cluster, such as N-acetylgalactosamine trimer. In some embodiments, the conjugate group comprises a GalNAc (N-acetylgalactosamine), such as a mono-valent, di-valent, tri-valent of tetra-valent GalNAc. Trivalent GalNAc conjugates may be used to target the compound to the liver (see e.g. U.S. Pat. No. 5,994,517 and Hangeland et al., Bioconjug Chem. 1995 November-December; 6(6):695-701, WO2009/126933, WO2012/089352, WO2012/083046, WO2014/118267, WO2014/179620, & WO2014/179445), see specific examples in FIG. 2. These GalNAc references and the specific conjugates used therein are hereby incorporated by reference. Suitably the GalNAc moiety used may be on the form of a reactive ester.

In some embodiments the GalNAc conjugate group used in the method of the invention is or comprises:

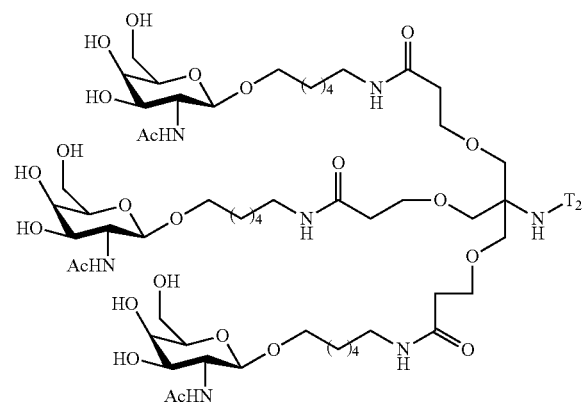

wherein $T_2$ is a reactive ester group.

In some embodiments the conjugate group is not lipophilic. In some embodiments the conjugate group is not a minor groove binding moiety. Minor groove binding molecules are usually constructed of a series of heterocyclic or aromatic hydrocarbon rings that possess rotational freedom. This allows the molecule to fit into the minor groove of a DNA double helix, with displacement of water. In some embodiments the conjugate group does not comprise:

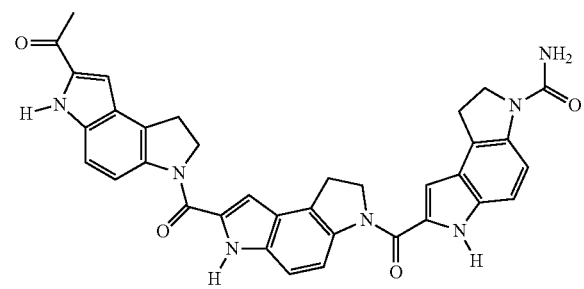 [SMILES: CC(=O)c1cc2c3c(ccc2[nH]1)N(C(=O)c1cc2c4c(ccc2[nH]1)N(C(=O)c1cc2c5c(ccc2[nH]1)N(C(N)=O)CC5)CC4)CC3]

Activated Ester

Activated esters are routinely used in organic chemistry as activating reagents for carboxylic acids. Activated acids then react with amines to form amides, for example.

In some embodiments, the conjugate group comprises an activated ester group, which is used to react to the amino group of the amino linker to form the oligonucleotide amide linked conjugate. In some embodiments the activated ester may be prepared in situ prior to conjugation, or may be prepared in a separate chemical reaction followed by purification. Suitable activated ester groups may, for example, be selected from the group consisting of a N-Hydroxysuccinimide (NHS) ester, sulfo-NHS ester, pentafluorophenyl (PFP) ester, sulfotetrafluorophenyl (STP) ester. O-acylisourea, hydroxybenzotriazole (HOBt) ester, 1-hydroxy-7-azabenzotriazole (HOAt) ester and an acid anhydride.

Molar Ratio of Conjugate Group/Oligonucleotide

One of the advantages of the method of the invention is the reduction in the amount of conjugate group required in the conjugation reaction, achieving a highly efficient conjugation of the oligonucleotide even when using a molar ratio of conjugate to oligonucleotide of less than 2. In some embodiments the molar ratio of conjugate group/oligonucleotide used is less than about 2, such as less than about 1.8, such as less than about 1.6, such as less than about 1.5, such as less than about 1.4, such as less than about 1.3, such as about less than about 1.2, such as less than about 1.1, such as about 1.

In some embodiments the molar ratio of conjugate group/oligonucleotide used is greater than about 0.25, such as greater than about 0.5, such as greater than about 0.75. In some embodiments the molar ratio of conjugate group/oligonucleotide used is between about 0.25-about 2, such as between about 0.5-about 2, such as between about 0.75-about 2. In some embodiments the molar ratio of conjugate group/oligonucleotide used is between about 0.25-about 1.5, such as between about 0.5-about 1.5, such as between about 0.75-about 1.5. In some embodiments the molar ratio of conjugate group/oligonucleotide used is between about 0.25-about 1.5, such as between about 0.5-about 1.5, such as between about 0.75-about 1.5. In some embodiments the molar ratio of conjugate group/oligonucleotide used is between about 0.25-about 1.25, such as between about 0.5-about 1.25, such as between about 0.75-about 1.25. In some embodiments the molar ratio of conjugate group/oligonucleotide used is between about 0.8-about 1.2, or between about 0.9 and about 1.1. In some embodiments stoichiometric amounts of conjugate group and oligonucleotide are used (i.e. a ratio of about 1)

Preparation of the Solvent Composition

The solvent composition may for example be prepared by the preliminary steps of
 a) providing an aqueous composition comprising an oligonucleotide comprising a reactive amino group
 b) adding an lipophillic salt to form an oligonucleotide salt precipitate;
 b) removing the water from the product of step b) to provide an reduced water, or essentially dry, composition,
 c) dissolving the reduced water or essentially dry composition obtained in step b) in a polar aprotic solvent, e.g. DMF or DMSO, to provide the solvent composition.

Water may be removed from the aqueous solvent using any suitable method known to the skilled person, for example by filtration with a solvent, evaporation e.g. in a vacuum vessel or by freeze drying, or centrifugal evaporation. In some embodiments the oligonucleotide is washed with a solvent such as butanol, acetonitrile, dioxane, THF or acetone, and may be collected by centrifugation or filtration. Additional water may be removed by additional washing steps using these solvents, and the washing solvent may then be removed by evaporation e.g. under vacuum. Water, or an alternative protic solvent (such as an alcohol, such as ethanol or methanol) may also be added to optimise the level of water/protic solvent for the conjugation step.

In some embodiments, the molar concentration of the aqueous solution of oligonucleotide in step a) is between about 0.1 mM and about 1M, such as between about 1 mM and about 100 mM, such as between about 10-about 20 mM.

In some embodiments, the molar concentration of the solvent solution of oligonucleotide in step c) is between about 0.1 mM and about 1M, such as between about 1 mM and about 100 mM, such as between about 10-about 20 mM.

In some embodiments, the molar concentration of the aqueous solution of oligonucleotide in step a) is between about 10 and about 20 mM oligonucleotide and about 5-10 mM, such as about 9 mM such as about 8.8 mM oligonucleotide in the solvent solution (e.g. DMF or DMSO).

Conversion Ratio

The conversion ratio is determined as a molar ratio of the amount of oligonucleotide conjugate as compared to the amount of oligonucleotide used in the reaction step. In some embodiments, the conversion ratio of oligonucleotide conjugate product from the oligonucleotide is at least about 50%, such as at least about 75%, such as least about 80%, such as at least about 85%, such as at least about 90%, such as at least about 95%.

Definitions

Nucleotides

Nucleotides are the building blocks of oligonucleotides and polynucleotides, and for the purposes of the present invention include both naturally occurring and non-naturally occurring nucleotides. In nature, nucleotides, such as DNA and RNA nucleotides comprise a ribose sugar moiety, a nucleobase moiety and one or more phosphate groups (which is absent in nucleosides). Nucleosides and nucleotides may also interchangeably be referred to as "units" or "monomers".

Modified Nucleoside

The term "modified nucleoside" or "nucleoside modification" as used herein refers to nucleosides modified as compared to the equivalent DNA or RNA nucleoside by the introduction of one or more modifications of the sugar moiety or the (nucleo)base moiety. In a preferred embodiment the modified nucleoside comprise a modified sugar moiety, and may for example comprise one or more 2' substituted nucleosides and/or one or more LNA nucleosides. The term modified nucleoside may also be used herein interchangeably with the term "nucleoside analogue" or modified "units" or modified "monomers".

Modified Internucleoside Linkage

The term "modified internucleoside linkage" is defined as generally understood by the skilled person as linkages other than phosphodiester (PO) linkages, that covalently couples two nucleosides together. Nucleotides with modified internucleoside linkage are also termed "modified nucleotides". In some embodiments, the modified internucleoside linkage increases the nuclease resistance of the oligonucleotide compared to a phosphodiester linkage. For naturally occurring oligonucleotides, the internucleoside linkage includes phosphate groups creating a phosphodiester bond between adjacent nucleosides. Modified internucleoside linkages are particularly useful in stabilizing oligonucleotides for in vivo use, and may serve to protect against nuclease cleavage at regions of DNA or RNA nucleosides in the oligonucleotide of the invention, for example within the gap region of a gapmer oligonucleotide, as well as in regions of modified nucleosides.

In an embodiment, the oligonucleotide comprises one or more internucleoside linkages modified from the natural phosphodiester to a linkage that is for example more resistant to nuclease attack. Nuclease resistance may be determined by incubating the oligonucleotide in blood serum or by using a nuclease resistance assay (e.g. snake venom phosphodiesterase (SVPD)), both are well known in the art. Internucleoside linkages which are capable of enhancing the nuclease resistance of an oligonucleotide are referred to as nuclease resistant internucleoside linkages. In some embodiments at least 50% of the internucleoside linkages in the oligonucleotide, or contiguous nucleotide sequence thereof, are modified, such as at least 60%, such as at least 70%, such as at least 80 or such as at least 90% of the internucleoside linkages in the oligonucleotide, or contiguous nucleotide sequence thereof, are modified. In some embodiments all of the internucleoside linkages of the oligonucleotide, or contiguous nucleotide sequence thereof, are modified. It will be recognized that, in some embodiments the nucleosides which link the oligonucleotide of the invention to a non-nucleotide functional group, such as a conjugate, may be phosphodiester. In some embodiments all of the internucleoside linkages of the oligonucleotide, or contiguous nucleotide sequence thereof, are nuclease resistant internucleoside linkages.

Modified internucleoside linkages may be selected from the group comprising phosphorothioate, diphosphorothioate and boranophosphate. In some embodiments, the modified internucleoside linkages are compatible with the RNaseH recruitment of the oligonucleotide of the invention, for example phosphorothioate, diphosphorothioate or boranophosphate. In some embodiments the internucleoside linkage comprises sulphur (S), such as a phosphorothioate internucleoside linkage. A phosphorothioate internucleoside linkage is particularly useful due to nuclease resistance, beneficial pharmakokinetics and ease of manufacture. In some embodiments at least 50% of the internucleoside linkages in the oligonucleotide, or contiguous nucleotide sequence thereof, are phosphorothioate, such as at least 60%, such as at least 70%, such as at least 80 or such as at least 90% of the internucleoside linkages in the oligonucleotide, or contiguous nucleotide sequence thereof, are phosphorothioate. In some embodiments all of the internucleoside linkages of the oligonucleotide, or contiguous nucleotide sequence thereof, are phosphorothioate.

In some embodiments, the oligonucleotide comprises one or more neutral internucleoside linkage, particularly a internucleoside linkage selected from phosphotriester, methylphosphonate, MMI, amide-3, formacetal or thioformacetal.

Further internucleoside linkages are disclosed in WO2009/124238 (incorporated herein by reference). In an embodiment the internucleoside linkage is selected from linkers disclosed in WO2007/031091 (incorporated herein by reference). Particularly, the internucleoside linkage may be selected from —O—P(O)$_2$—O—, —O—P(O,S)—O—, —O—P(S)$_2$—O—, —S—P(O)$_2$—O—, —S—P(O,S)—O—, —S—P(S)$_2$—O—, —O—P(O)$_2$—S—, —O—P(O,S)—S—, —S—P(O)$_2$—S—, —O—PO(R$^H$)—O—, 0-PO(OCH$_3$)-0-, —O—PO(NR$^H$)—O—, —O—PO(OCH$_2$CH$_2$S—R)—O—, —O—PO(BH$_3$)—O—, —O—PO(NHR$^H$)—O—, —O—P(O)$_2$NR$^H$—, —NR$^H$—P(O)$_2$—O—, —NR$^H$—CO—O—, —NR$^H$—CO—NR$^H$—, and/or the internucleoside linker may be selected form the group consisting of: —O—CO—O—, —O—CO—NR$^H$—, —NR$^H$—CO—CH$_2$—, —O—CH$_2$—CO—NR$^H$—, —O—CH$_2$—CH$_2$—NR$^H$—, —CO—NR$^H$—CH$_2$—, —CH$_2$NR$^H$CO—, —O—CH$_2$—CH$_2$—S—, —S—CH$_2$—CH$_2$—O—, —S—CH$_2$—CH$_2$—S—, —CH$_2$—SO$_2$—CH$_2$—, —CH$_2$CO—NR$^H$—, —O—CH$_2$—CH$_2$—NR$^H$ CO—, —CH$_2$—NCH$_3$—O—CH$_2$—, where R$^H$ is selected from hydrogen and C1-4-alkyl.

Nuclease resistant linkages, such as phosphothioate linkages, are particularly useful in oligonucleotide regions capable of recruiting nuclease when forming a duplex with the target nucleic acid, such as region G for gapmers, or the non-modified nucleoside region of headmers and tailmers. Phosphorothioate linkages may, however, also be useful in non-nuclease recruiting regions and/or affinity enhancing regions such as regions F and F for gapmers, or the modified nucleoside region of headmers and tailmers.

Each of the design regions may however comprise internucleoside linkages other than phosphorothioate, such as phosphodiester linkages, in particular in regions where modified nucleosides, such as LNA, protect the linkage against nuclease degradation. Inclusion of phosphodiester linkages, such as one or two linkages, particularly between or adjacent to modified nucleoside units (typically in the non-nuclease recruiting regions) can modify the bioavailability and/or bio-distribution of an oligonucleotide—see WO2008/113832, incorporated herein by reference.

In an embodiment all the internucleoside linkages in the oligonucleotide are phosphorothioate and/or boranophosphate linkages. Preferably, all the internucleoside linkages in the oligonucleotide are phosphorothioate linkages.

Nucleobase

The term nucleobase includes the purine (e.g. adenine and guanine) and pyrimidine (e.g. uracil, thymine and cytosine) moiety present in nucleosides and nucleotides which form hydrogen bonds in nucleic acid hybridization. In the context of the present invention the term nucleobase also encompasses modified nucleobases which may differ from naturally occurring nucleobases, but are functional during nucleic acid hybridization. In some embodiments the nucleobase moiety is modified by modifying or replacing the nucleobase.

In this context "nucleobase" refers to both naturally occurring nucleobases such as adenine, guanine, cytosine, thymidine, uracil, xanthine and hypoxanthine, as well as non-naturally occurring variants. Such variants are for example described in Hirao et al (2012) Accounts of Chemical Research vol 45 page 2055 and Bergstrom (2009) Current Protocols in Nucleic Acid Chemistry Suppl. 37 1.4.1.

In a some embodiments the nucleobase moiety is modified by changing the purine or pyrimidine into a modified purine or pyrimidine, such as substituted purine or substituted pyrimidine, such as a nucleobase selected from isocytosine, pseudoisocytosine, 5-methyl cytosine, 5-thiozolo-cytosine, 5-propynyl-cytosine, 5-propynyl-uracil, 5-bromouracil 5-thiazolo-uracil, 2-thio-uracil, 2'thio-thymine, inosine, diaminopurine, 6-aminopurine, 2-aminopurine, 2,6-diaminopurine and 2-chloro-6-aminopurine.

The nucleobase moieties may be indicated by the letter code for each corresponding nucleobase, e.g. A, T, G, C or U, wherein each letter may optionally include modified nucleobases of equivalent function. For example, in the exemplified oligonucleotides, the nucleobase moieties are selected from A, T, G, C, and 5-methyl cytosine. Optionally, for LNA gapmers, 5-methyl cytosine LNA nucleosides may be used.

LNA Oligonucleotides

An LNA oligonucleotide is an oligonucleotide which comprises at least one LNA nucleoside.

The invention therefore relates to methods of preparing LNA antisense oligonucleotide conjugates. The LNA oligonucleotide may be an antisense oligonucleotide.

The term oligonucleotide as used herein is defined as it is generally understood by the skilled person as a molecule comprising two or more covalently linked nucleosides. For use as an antisense oligonucleotide, oligonucleotides are typically synthesised as 7-30 nucleotides in length. LNA antisense oligonucleotides typically comprise one or more modified internucleoside linkages, and may by way of a non-limiting example be in the form of a LNA gapmer or a mixed wing gapmer. In some embodiments the oligonucleotide may be an LNA mixmers (LNA and non-LNA nucleotides, e.g. LNA and DNA (see e.g. WO2007/112754 hereby incorporated by reference), or LNA and 2'-O-MOE nucleotides, or LNA, DNA and 2'O-MOE nucleotides), or a LNA totalmers (only LNA nucleotides—see. E.g. WO2009/043353 hereby incorporated by reference).

Linkers

A linkage or linker is a connection between two atoms that links one chemical group or segment of interest to another chemical group or segment of interest via one or more covalent bonds. Conjugate moieties can be attached to the oligonucleotide directly or through a linking moiety (e.g. linker or tether). Linkers serve to covalently connect a third region. e.g. a conjugate group to a first region, e.g. an oligonucleotide (region A).

In the context of the present invention the linker may comprise the amino group, such as the aliphatic amino group, such as a primary or secondary aliphatic amino group. In some embodiments the linker is an aliphatic amino alkyl, such as a C$_2$-C$_{36}$ aliphatic amino alkyl group, including, for example C$_6$ to C$_{12}$ aliphatic amino alkyl groups. In some embodiments the linker is a C$_6$ aliphatic amino alkyl group. In some embodiments the oligonucleotide comprises a region of DNA phosphodiester nucleotides, e.g. 1-5 DNA PO nucleotides which are positioned between the antisense oligonucleotide and the aliphatic amino linker, e.g. at the 5' or 3' end of the oligonucleotide—see WO2014/076195 hereby incorporated by reference.

Locked Nucleic Acid Nucleosides (LNA)

In some embodiments the oligonucleotide comprises one or more LNA nucleosides. LNA nucleosides are modified nucleosides which comprise a linker group (referred to as a biradicle or a bridge) between C2' and C4' of the ribose sugar ring of a nucleotide. These nucleosides are also termed bridged nucleic acid or bicyclic nucleic acid (BNA) in the literature.

Exemplary LNA nucleosides include those shown in FIG. 1:

Scheme 1

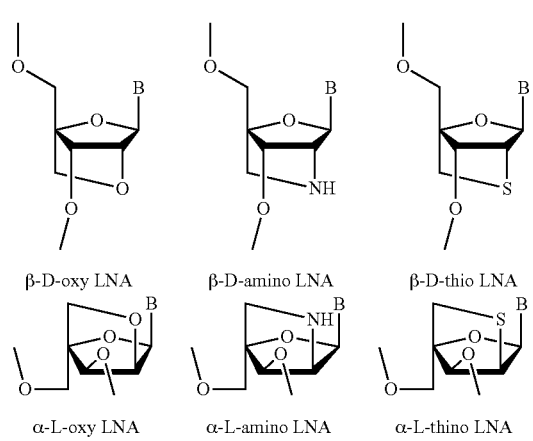

β-D-oxy LNA    β-D-amino LNA    β-D-thio LNA

α-L-oxy LNA    α-L-amino LNA    α-L-thino LNA

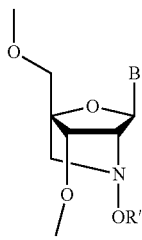
β-D-amino substituted LNA

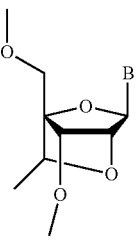
6′ methyl β-D-oxy LNA

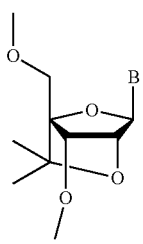
6′ dimethyl β-D-oxy LNA

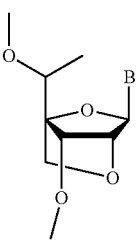
5′ methyl β-D-oxy LNA

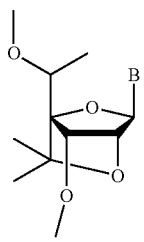
5′ methyl, 6′dimethyl β-D-oxy LNA

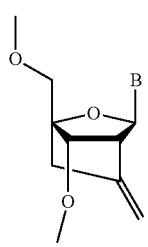
Carbocyclic(vinyl) β-D- LNA

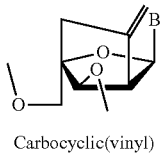
Carbocyclic(vinyl) α-L- LNA

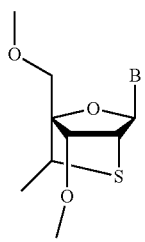
6′ methyl thio β-D LNA

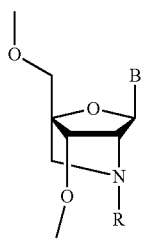
Substituted β-D amino LNA

As illustrated in the examples, in some embodiments of the invention the LNA nucleosides in the oligonucleotides are or comprise beta-D-oxy-LNA nucleosides.

Gapmer

The term gapmer as used herein refers to an antisense oligonucleotide which comprises a region of RNase H recruiting oligonucleotides (gap) which is flanked 5′ and 3′ by one or more affinity enhancing modified nucleosides (flanks). Various gapmer designs are described herein. Headmers and tailmers are oligonucleotides capable of recruiting RNase H where one of the flanks are missing, i.e. only one of the ends of the oligonucleotide comprises affinity enhancing modified nucleosides. For headmers the 3′ flank is missing (i.e. the 5′ flank comprise affinity enhancing modified nucleosides) and for tailmers the 5′ flank is missing (i.e. the 3′ flank comprises affinity enhancing modified nucleosides).

LNA Gapmer

The term LNA gapmer is a gapmer oligonucleotide wherein at least one of the affinity enhancing modified nucleosides is an LNA nucleoside. In some embodiments, the oligonucleotide used in the method of the invention is a LNA gapmer.

Mixed Wing Gapmer

The term mixed wing gapmer refers to a LNA gapmer wherein the flank regions comprise at least one LNA nucleoside and at least one non-LNA modified nucleoside, such as at least one 2′ substituted modified nucleoside, such as, for example, 2′-O-alkyl-RNA, 2′-O-methyl-RNA, 2′-alkoxy-RNA, 2′-O-methoxyethyl-RNA (MOE), 2′-amino-DNA, 2′-Fluoro-DNA, arabino nucleic acid (ANA), 2′-fluoro-ANA and 2′-F-ANA nucleoside(s). In some embodiments the mixed wing gapmer has one flank which comprises LNA nucleosides (e.g. 5′ or 3′) and the other flank (3′ or 5′ respectfully) comprises 2′ substituted modified nucleoside(s).

Length

When referring to the length of a nucleotide molecule as referred to herein, the length corresponds to the number of monomer units, i.e. nucleotides, irrespective as to whether those monomer units are nucleotides or nucleotide analogues. With respect to nucleotides, the terms monomer and unit are used interchangeably herein.

The process of the present invention is particularly suitable for the preparation of short oligonucleotide conjugates, for example, consisting of 7 to 30 nucleotides, such as 7-10, such as 7, 8, 9, 10 or 10 to 20 nucleotides, such as 12 to 18 nucleotides, for example, 12, 13, 14, 15, 16, 17 or 18 nucleotides.

EXAMPLES

Unless otherwise indicated, the examples were performed at room temperature of 20-25° C. eq=equivalents, and is the molar ratio.

The aminolabelled oligonucleotide used in the examples was

5′-AM-C6$_s$G$_s$T$_s$t$_s$g$_s$a$_s$c$_s$a$_s$c$_s$t$_s$g$_s$T$_s$$^m$C-3 (SEQ ID NO 4).

wherein uppercase letters denote bet-D-oxy-LNA units; lowercase letters denote DNA units; the subscript "s" denotes a phosphorothioate linkage; superscript m denotes a DNA or beta-D-oxy-LNA unit containing a 5-methylcytosine base. AM-C6 is an amino hexyl linker.

The molar mass of the sodium salt of the oligonucleotide is 4398.3 g/mol. The molar mass of the CTA sat of the oligonucleotide is 7536.9 g/mol.

The conversion of aminolabelled oligonucleotide and conjugate group to conjugated oligonucleotide (also termed conjugate) was determined as the area under the conjugate peak divided by the total area under the peaks of the conjugate and aminolabelled oligonucleotide.

Example 1 Formation of CTA Salt of Oligonucleotide from Sodium Salt

Method 1: Using Solid CTACl

To a solution of aminolabelled oligonucleotide (250 mg, 56.8 μmol) in 2.5 mL water, was added cetyltrimethylammonium chloride (CTACl) (220 mg, 688 μmol) while stirring. This amount corresponds to 1 equivalent per "phosphate" group present in the oligonucleotide. (12 phosphorothiate groups were present 688 μmol/(56.8 mmol*12)=1.01). The addition of CTACl caused precipitation of the desired cetyltrimethylammonium salt of the oligonucleotide to occur. The precipitate was isolated by centrifugation, and washed with water. The solid was dried by lyophilization overnight. The isolated yield of CTA salt of oligonucleotide was 414 mg, corresponding to a yield of 97%.

The supernatant was essentially free of aminolabelled oligonucleotide as determined by UV absorbance at 260 nm, indicating that all oligonucleotide had precipitated as the CTA salt.

Method 2: Using an Aqueous Solution of CTACl

To a solution of aminolabelled oligonucleotide (250 mg, 56.8 μmol) in 2.5 mL water, was added an aqueous solution of cetyltrimethylammonium chloride (CTACl) (220 mg, 688 μmol) in 1 mL water while stirring. This amount corresponds to 1 equivalent per "phosphate" group present in the oligonucleotide. (12 phosphorothiate groups were present: 688 μmol/(56.8 mmol*12)=1.01). The addition of the CTACl solution caused precipitation of the desired cetyltrimethylammonium salt of the oligonucleotide to occur. The precipitate was isolated by centrifugation, and hereafter washed with water. The solid was dried by lyophilization overnight. The isolated yield of CTA salt of oligonucleotide was 419 mg corresponding to a yield of 98%.

The supernatant was essentially free of oligonucleotide as determined by UV absorbance at 260 nm, indicating that all oligonucleotide had precipitated as the CTA salt.

Method 2 is preferred, as precipitation is more easily handled, as the CTACl is already in solution, and does not need to be brought into solution at the same time that the oligonucleotide CTA salt is precipitating.

Example 2 Preparation of GalNAc2 NHS Ester

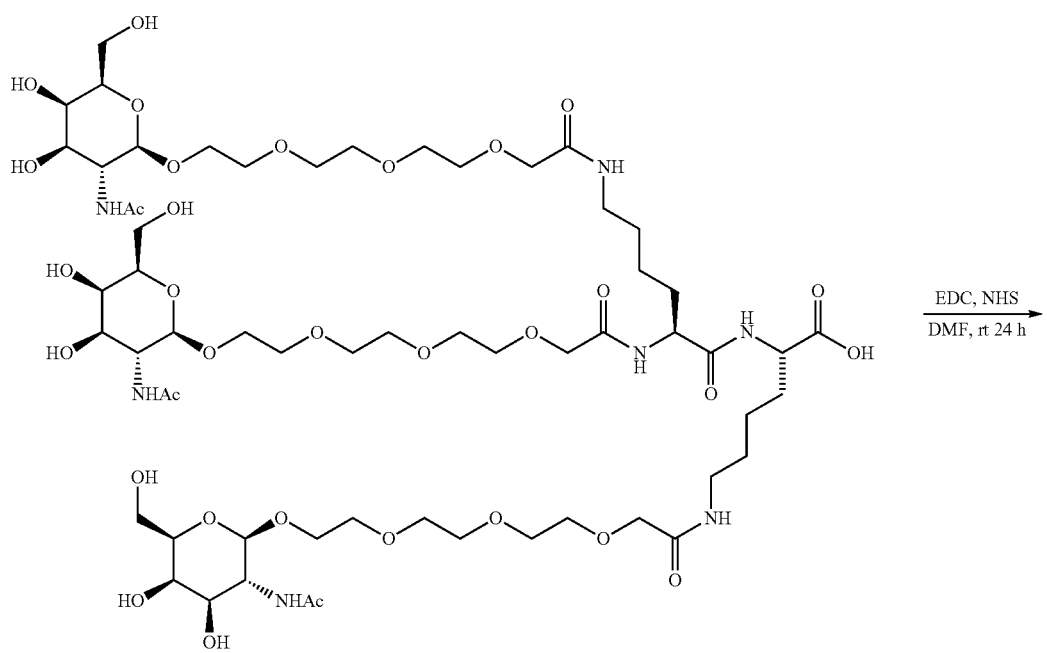

-continued

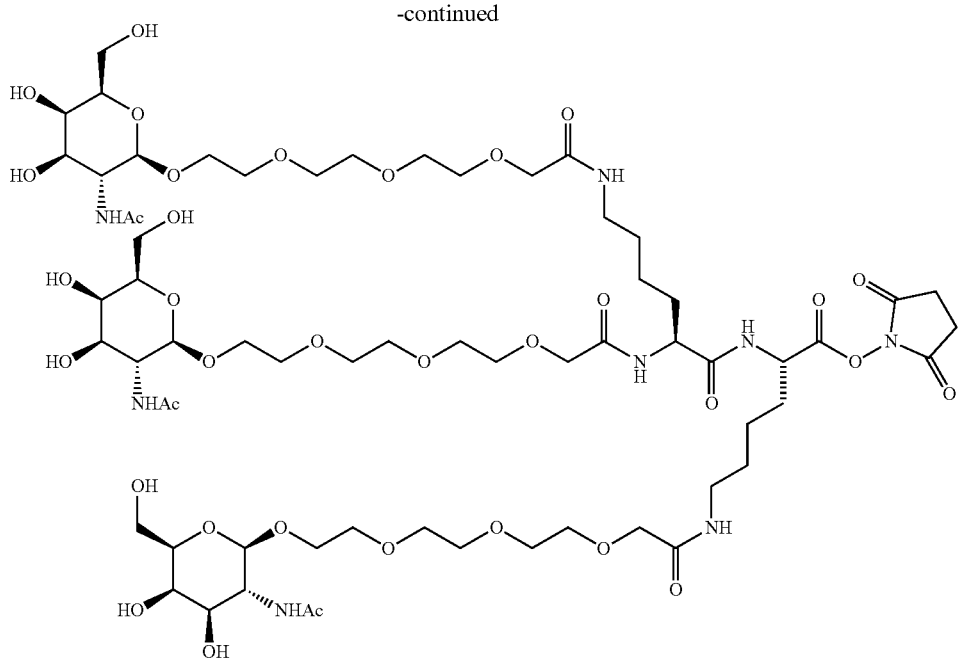

To a solution of the carboxylic acid of GalNAc2 (45 mg, 31 µmol) in DMF (0.9 mL), N-hydroxysuccinimide (NHS) (3.9 mg, 34 µmol) and N-(3-Dimethytaminopropyl)-N'-ethylcarbodiimide hydrochloride (EDC)(6.5 mg, 34 µmol) were added. The solution was left to react for 16 h, and used directly for oligonucleotide conjugation.

Example 3 Conjugation of GalNAc2 NHS Ester to Aminolabelled Oligonucleotide Sodium Salt in Aqueous Solution To a solution of aminolabelled oligonucleotide sodium salt (4.4 mg, 10 µmol) in 100 µL 20 mM $NaHCO_3$ buffer (pH 8.5), was added diisopropylethylamine (1.8 µL, 10 µmol, 10 eq), and the desired equivalents of GalNAc2 NHS ester, from a stock solution of 34 mM (prepared as described in example 2), as shown in table 1 below. The reaction was allowed to proceed for 2 h, where after the reaction mixture was analyzed by reversed phase LC-MS.

TABLE 1

Equivalents of aminolabelled oligonucleotide in water and GalNAc2 NHS ester
GalNAc2 NHS ester
(34 mM in DMF)

| Equivalents | Volume (µL) | Conversion after 2 h |
|---|---|---|
| 1 | 30 µL (1.02 µmol) | 49% |
| 2 | 60 µL (2.04 µmol) | 95% |
| 3 | 90 µL (3.06 µmol) | 100% |

As shown in FIG. 3, if the oligonucleotide was dissolved in water only, there was a need for at least a two times molar excess of the NHS ester relative to the aminolabelled oligonucleotide.

Example 4 Conjugation of GalNAc2 NHS Ester to Aminolabelled Oligonucleotide CTA Salt in N,N-Dimethylformamide Solution A stock solution of aminolabelled oligonucleotide CTA salt (prepared according to example 1 method 2) (100 mg, 13.2 µmol) in 1.5 mL anhydrous N,N-dimethylformamide (DMF) was prepared, to yield a solution with a concentration of 8.8 mM.

To 100 µL of this solution of aminolabelled oligonucleotide CTA salt (0.88 µmol) was added diisopropylethylamine (DIPEA) (1.4 µL, 7.9 µmol, 9 eq.), and the desired amount of GalNAc2 N-hydroxysuccinimide (NHS) ester from a stock solution in DMF at a concentration of 34 mM (prepared as described in example 2), as described in table 2 below. The reaction was allowed to proceed for up to 24 h. The reaction was analyzed after 1 h, 2 h and 24 h. The conjugation efficacy was analyzed by reversed phase LC-MS. The results are shown graphically in FIG. 4 Conversion ratios are seen to correlate with the molar equivalent of conjugate group used compared to oligonucleotide, thus a 100% conversion of conjugate group to oligonucleotide conjugate was achieved. It is seen that the conversion correspond to the molar equivalent used, and is thus a significant improvement compared to example 3.

TABLE 2

Equivalents of aminolabelled oligonucleotide in DMF and GalNAc2 NHS ester
GalNAc2 NHS ester
(34 mM in DMF)

| Equivalents | Volume (µL) | Conversion after 2 h |
|---|---|---|
| 0.44 | 11.5 µL (0.39 µmol) | 45% |
| 0.89 | 23 µL (0.78 µmol) | 83% |
| 1.78 | 46 µL (1.56 µmol) | 100% |

Example 5 Conjugation of Digoxigenin NHS Ester to Aminolabelled Oligonucleotide CTA Salt in N,N-Dimethylformamide Solution A stock solution of aminolabelled oligonucleotide CTA salt (100 mg, 13.2 µmol) in 1.5 mL anhydrous N,N-dimethylformamide (DMF) was prepared as described in Example 4.

To 100 µL of this solution of aminolabelled oligonucleotide CTA salt (0.88 µmol) was added diisopropylethylamine (DIPEA) (1.4 µL, 7.9 µmol, 9 eq.), and the desired amount of digoxigenin N-hydroxysuccinimide (NHS) ester from a stock solution in DMF at a concentration of 40 mM, as described in table 3 below. The reaction was allowed to proceed for 2 h. The reaction was analyzed after 2 h. The conjugation efficacy was analyzed by reversed phase LC-MS. The results are shown graphically in FIG. 5. Conversion ratios are seen to correlate with the molar equivalent of conjugate group used compared to oligonucleotide, thus a 100% conversion of conjugate group to oligonucleotide conjugate was achieved. It is seen that the conversion correspond to the molar equivalent used. This experiment employs a different NHS ester than example 4, and thus results in a different conjugate type (digoxigenin). This confirms that the reaction conditions are broadly applicable.

TABLE 3

Equivalents of aminolabelled oligonucleotide in DMF and digoxigenin NHS ester Digoxigenin NHS ester (40 mM in DMF)

| Equivalents | Volume (µL) | Conversion after 2 h |
|---|---|---|
| 0.45 | 10 (0.40 µmol) | 49% |
| 0.91 | 20 (0.80 µmol) | 88% |
| 1.82 | 40 (1.6 µmol) | 100% |

Example 6 Conjugation of Fluorescein NHS Ester to Aminolabelled Oligonucleotide CTA Salt in N,N-dimethylformamide Solution A stock solution of aminolabelled oligonucleotide CTA salt (100 mg, 13.2 µmol) in 1.5 mL anhydrous N,N-dimethylformamide (DMF) was prepared as described in Example 4.

To 100 µL of this solution of aminolabelled oligonucleotide CTA salt (0.88 µmol) was added diisopropylethylamine (DIPEA) (1.4 µL, 7.9 µmol, 9 eq.), and the desired amount of fluorescein N-hydroxysuccinimide (NHS) ester from a stock solution in DMF at a concentration of 40 mM, as described in table 4 below. The reaction was allowed to proceed for 2 h. The reaction was analyzed after 2 h. The conjugation efficacy was analyzed by reversed phase LC-MS. The results are shown graphically in FIG. 6. Conversion ratios are seen to correlate with the molar equivalent of conjugate group used compared to oligonucleotide, thus a 100% conversion of conjugate group to oligonucleotide conjugate was achieved. It is seen that the conversion correspond to the molar equivalent used. This experiment employs a different NHS ester than example 4 and 5, and thus results in a different conjugate type (fluorescein). This confirms that the reaction conditions are broadly applicable.

TABLE 4

Equivalents of aminolabelled oligonucleotide in DMF and Fluorescein NHS ester Fluorescein NHS ester (40 mM in DMF)

| Equivalents | Volume (µL) | Conversion after 2 h |
|---|---|---|
| 0.45 | 10 (0.40 µmol) | 56% |
| 0.91 | 20 (0.80 µmol) | 88% |
| 1.82 | 40 (1.6 µmol) | 100% |

Example 7 Formation of Sodium Salt of Oligonucleotide from CTA Salt

After the conjugation reaction has completed, the oligonucleotide was precipitated as the sodium salt using one of two methods, to allow for purification by routine methods, such as anion exchange chromatography or reversed phase chromatography Method 1) Using an Aqueous Solution of NaCl and Ethanol To 1 mL of the DMF solution of conjugated oligonucleotide CTA salt (e.g. as prepared in examples 4 to 6) was added 0.2 mL of an aqueous solution of NaCl (2M), followed by ethanol (5 mL), which caused the sodium salt of the oligonucleotide to precipitate. The precipitate was recovered using centrifugation.

Method 2) Using 2% NaClO4 (w/v) in Acetone

To 1 mL of the DMF solution of conjugated oligonucleotide CTA salt (e.g. as prepared in examples 4 to 6) was added 2% NaClO4 (w/v) in acetone (5 mL), which caused the sodium salt of the oligonucleotide to precipitate. The precipitate was recovered using centrifugation.

Example 8 Comparison of Conversions of CTA Salt and TEA Salt of Aminolabelled Oligonucleotide to GalNAc2 Conjugate in Anhydrous N,N-dimethylformamide and in Anhydrous Dimethylsulfoxide after 1 h The triethylammonium (TEA) salt of the aminolabelled oligonucleotide was prepared according to the procedure by Milesi et.al. (Methods in Enzymology (1999) 313, pp 164-173). Solutions of the TEA salt were prepared in a concentration at 8.8 mM In respectively anhydrous DMF and anhydrous DMSO.

Solutions of the CTA salt were prepared in a concentration at 8.8 mM in respectively anhydrous DMF and anhydrous DMSO.

A solution of GalNAc2 NHS ester was prepared in a concentration at 34 mM in DMF as described in example 2.

Four reactions were prepared according to the following general protocol employing the solutions prepared, as stated above.

To 100 µL of the solution of aminolabelled oligonucleotide (0.88 µmol) was added diisopropylethylamine (DIPEA) (1.4 µL, 7.9 µmol, 9 eq.), GalNAc2 N-hydroxysuccinimide (NHS) ester (26 µL, 0.884 µmol). The reaction was analyzed after 1 h. The conjugation efficacy was analyzed by reversed phase LC-MS. The results are shown in FIG. 7 and in table 5 below.

It is seen that the conversion of the CTA salt after 1 hour is higher than for the TEA salt. The effect is particularly pronounced when employing DMSO as the solvent, indicating that the conversion rate for the CTA salt is higher than for the TEA salt in general, and furthermore that DMF as solvent results in higher reaction rates.

After 24 h reaction time, full conversion was observed in all cases.

TABLE 5

Conversion of aminolabelled oligonucleotide CTA salt and TEA salt reacted with GalNAc2 NHS ester. Conversions after 1 h

| Solvent | Conversion (CTA salt) | Conversion (TEA salt) |
|---|---|---|
| DMF | 92% | 88% |
| DMSO | 78% | 60% |

Example 9—the Effect of Water Content on the Efficacy of Oligonucleotide Conjugation A stock solution of aminolabelled oligonucleotide CTA salt (100 mg, 13.2 µmol) in 1.5 mL anhydrous N,N-dimethylformamide (DMF) was prepared, to yield a solution with a concentration of 8.8 mM.

A solution of GalNAc 2 NHS ester was prepared in a concentration at 34 mM in DMF as described in example 2.

Ten reaction mixtures with a varying amount of water were prepared according to table 6 below.

To 40 µL of the solution of aminolabelled oligonucleotide CTA salt (0.35 µmol) was added water according to the table below, diisopropylethylamine (DIPEA) (0.6 µL 3.4 µmol, 10 eq.), and GalNAc2 N-hydroxysuccinimide (NHS) ester (9.5 µL, 0.32 µmol). The reaction was allowed to proceed for 24 h.

Hereafter the reaction mixture was diluted with 0.5 mL DMF to ensure full homogeneity of the samples. The oligonucleotides were precipitated from the reaction mixtures using 2.5 mL 2% $NaClO_4$, and recovered by centrifugation. The obtained pellet was dissolved in 1 mL $H_2O$ and analysed by reversed phase LC-MS. The results are shown in FIG. 8 and in table 6 below. It can be seen that conversion of 85% or above can be achieved with up to 14% water in the reaction mixture. This is an advantage since the solutions used in the reaction do not need to be 100% anhydrous.

TABLE 6

Conversion of aminolabelled oligonucleotide CTA salt reacted with GalNAc2 NHS in varying amounts of water.

| Vol Oligo (µL) | Vol NHS ester (µL) | Vol DIPEA (µL) | Vol Water (µL) | Vol % water of reaction mixture | Conversion |
|---|---|---|---|---|---|
| 40 | 9.5 | 0.6 | 0 | 0.0% | 94.2% |
| 40 | 9.5 | 0.6 | 1 | 1.9% | 96.6% |
| 40 | 9.5 | 0.6 | 2 | 3.8% | 96.3% |
| 40 | 9.5 | 0.6 | 4 | 7.3% | 97.9% |
| 40 | 9.5 | 0.6 | 6 | 10.6% | 94.6% |
| 40 | 9.5 | 0.6 | 8 | 13.7% | 85.0% |
| 40 | 9.5 | 0.6 | 12 | 19.2% | 51.6% |
| 40 | 9.5 | 0.6 | 16 | 24.0% | 31.8% |
| 40 | 9.5 | 0.6 | 20 | 28.3% | 22.1% |
| 40 | 9.5 | 0.6 | 40 | 44.2% | 1.0% |

The invention claimed is:

1. A process of synthesizing an amide linked oligonucleotide conjugate comprising the step of reacting a conjugate group to a reactive amino group of an oligonucleotide, wherein said reaction step is performed in a solvent composition comprising at least about 85% (v/v) polar aprotic solvent, wherein the molar ratio of the conjugate group/oligonucleotide used in the solvent composition is between about 0.5 and about 2, and wherein the solvent composition comprises a lipophilic cation.

* * * * *

SEQUENCE LISTING

<160> NUMBER OF SEQ ID NOS: 4

<210> SEQ ID NO 1
<211> LENGTH: 15
<212> TYPE: DNA
<213> ORGANISM: Artificial
<220> FEATURE:
<223> OTHER INFORMATION: Oligonucleotide nucleobase sequence

<400> SEQUENCE: 1
cagcgtaaag agagg          15

<210> SEQ ID NO 2
<211> LENGTH: 16
<212> TYPE: DNA
<213> ORGANISM: Artificial
<220> FEATURE:
<223> OTHER INFORMATION: Oligonucleotide nucleobase sequence

<400> SEQUENCE: 2
cagcgtaaag agaggt          16

<210> SEQ ID NO 3
<211> LENGTH: 15

```
<212> TYPE: DNA
<213> ORGANISM: Artificial
<220> FEATURE:
<223> OTHER INFORMATION: Oligonucleotide nucleobase sequence

<400> SEQUENCE: 3
cagcgtaaag agagg                                              15

<210> SEQ ID NO 4
<211> LENGTH: 12
<212> TYPE: DNA
<213> ORGANISM: Artificial
<220> FEATURE:
<223> OTHER INFORMATION: Oligonucleotide nucleobase sequence

<400> SEQUENCE: 4
gttgacactg tc                                                 12
```